(12) United States Patent
Vailaya et al.

(10) Patent No.: US 7,519,605 B2
(45) Date of Patent: Apr. 14, 2009

(54) SYSTEMS, METHODS AND COMPUTER READABLE MEDIA FOR PERFORMING A DOMAIN-SPECIFIC METASEARCH, AND VISUALIZING SEARCH RESULTS THEREFROM

(75) Inventors: Aditya Vailaya, Santa Clara, CA (US); Allan J. Kuchinsky, San Francisco, CA (US); Robert H. Kincaid, Half Moon Bay, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 397 days.

(21) Appl. No.: 11/166,696

(22) Filed: Jun. 24, 2005

(65) Prior Publication Data
US 2005/0278321 A1 Dec. 15, 2005

Related U.S. Application Data

(63) Continuation-in-part of application No. 10/784,523, filed on Feb. 23, 2004, and a continuation-in-part of application No. 10/642,376, filed on Aug. 14, 2003, now Pat. No. 7,228,302, and a continuation-in-part of application No. 10/641,492, filed on Aug. 14, 2003, and a continuation-in-part of application No. 10/155,304, filed on May 22, 2002, now Pat. No. 7,058,643, and a continuation-in-part of application No. 10/154,524, filed on May 22, 2002, and a continuation-in-part of application No. 10/154,529, filed on May 22, 2002, now Pat. No. 7,155,453, and a continuation-in-part of application No. 10/155,616, filed on May 22, 2002, and a continuation-in-part of application No. 10/155,405, filed on May 22, 2002, now abandoned, which is a continuation-in-part of application No. 10/033,823, filed on Dec. 19, 2001, now Pat. No. 6,920,448, which is a continuation-in-part of application No. 09/863,115, filed on May 22, 2001, now abandoned.

(60) Provisional application No. 60/289,927, filed on May 9, 2001.

(51) Int. Cl.
*G06F 17/30* (2006.01)

(52) U.S. Cl. .......................... 707/100; 707/5; 707/102
(58) Field of Classification Search ................. 707/2–5, 707/100, 102
See application file for complete search history.

(56) References Cited

U.S. PATENT DOCUMENTS 5,732,221 A 3/1998 Feldon et al.

(Continued)

FOREIGN PATENT DOCUMENTS

| WO | WO 01/13105 | 2/2001 |
|---|---|---|
| WO | WO 02/027533 | 10/2002 |

OTHER PUBLICATIONS

Northern Light: "Startpage", Internet Artile [online] 2003, XP002388145. Retrieved from the Internet: URL: http://www.northernlight.com.

(Continued)

*Primary Examiner*—Cheryl Lewis

(57) ABSTRACT

Systems, methods and computer readable media for performing a domain-specific metasearch, and obtaining search results therefrom. A metasearch engine capable of accessing generic, web-based search engines and domain-relevant search engines is provided to receive one or more queries inputted by a user, and to search for documents on at least one the generic, web-based search engines and domain-relevant search engines which are relevant to the queries. Raw data search results are fetched in the form of text documents. Relevant data including semantic information are extracted from the raw data search results, and converted to a local format. The relevant data having been converted to the local format may be visualized as a network visualization. Additionally or alternatively, the raw data search results may be ranked and/or filtered based on the linking of the relevant data. Visualization of the raw data having been ranked and/or filtered may be performed in addition to, or alternative to visualization of the network.

25 Claims, 16 Drawing Sheets

U.S. PATENT DOCUMENTS

| | | | |
|---|---|---|---|
| 5,793,970 | A * | 8/1998 | Fakes et al. .................. 709/216 |
| 5,808,918 | A | 9/1998 | Fink et al. |
| 5,924,090 | A | 7/1999 | Krellenstein |
| 5,970,500 | A | 10/1999 | Sabatini et al. |
| 6,067,552 | A | 5/2000 | Yu |
| 6,078,739 | A | 6/2000 | Paterson et al. |
| 6,085,186 | A | 7/2000 | Christianson et al. |
| 6,102,969 | A | 8/2000 | Christianson et al. |
| 6,275,820 | B1 | 8/2001 | Navin-Chandra et al. |
| 6,363,399 | B1 | 3/2002 | Maslyn et al. |
| 6,496,832 | B2 | 12/2002 | Chi et al. |
| 6,694,482 | B1 | 2/2004 | Arellano et al. |
| 2002/0169764 | A1 | 11/2002 | Kincaid et al. |
| 2002/0178184 | A1 | 11/2002 | Kuchinsky et al. |

OTHER PUBLICATIONS

University of Washington/Department of Computer Science & Engineering: "Huskysearch", Internet article, [online] 2001, XP002388146. Retrieved from the Internet: www.cs.washington. edu/research projects/webWare1/www/metacrawler.

Visisimo "Startpage", internet article, [online] 2000, XP0022388147. Retrieved from the Internet: URL: http://vivisimo.com.

Searchlight/California Digital Library: "Startpage", Internet Article, [Online] 2005, XP..2388148. Retrieved from the Internet: URL:http://searchlight.cdib.org, no date.

Highbeam Research: "Startpage" Internet Article, [Online] XP002388149. Retrieved from the Internet: URL:http://www.highbeam.com, no date.

Bio-Crawler/Nias DNA Bank: "startpage" Internet Article, [Online] XP002388150. Retrieved from the Internet: URL;http://bio-crawler.dna.affrc.go.jp/, no date.

NLM Gateway Search: "Startpage", Internet Article, [Online] XP002388151, US Retrieved from the Internet: URL:http://gateway.nlm.nih.gov, no date.

Livelink ECM/Federated Query Server: "Startpage", Internet Article, [Online] XP002388152. Retrieved from the Internet: URL:http://www.queryserver.com, no date.

U.S. Appl. No. 10/155,675, filed May 22, 2002, pending.

Fukuda,Ken-Ichiroet al. Knowledge Representation of Signal Transduction Pathways, vol. 17, No. 9,2001, pp. 829-837.

Friedman, Nir et al. Using Bayesian Networks to Analyze Expression Data., 2000.

Milo,R. et al. Network Motifs: Simple Building Blocks of complex Networks., Science, vol. 298, Oct. 25, 2002.

Lee,Tong Ihn et al. Transcriptional Regulatory Networks in *Saccharomyces cerevisiae.*, Science,vol. 298, Oct. 25, 2002.

Shen-Orr,Shai S. et al. Networks Motifs in the Transcriptional Regulation Network of *Escherichia coli.*, Nature Genetics, vol. 31, May 2002.

NetBuilder. http://strc.herts.ac.uk/bio/maria/NetBuilder, downloaded Feb. 23, 2004.

JDesigner-A Biochemical Network Layout Tool. http://www.cds.caltech.edu/hsauro/JDesigner.htm, downloaded Feb. 23, 2004.

PC Magazine Editors' Choice: Visio 2003. http://www.microsoft.com/office/visio, downloaded Feb. 23, 2004.

Cadence Encounter RTL Compiler Now Supports VHDL—Global Synthesis for Highest Quality of Silicon.http://www.cadence.com/datasheets/virtuoso_layout_editor.html, downloaded Feb. 23, 2004.

The Signaling PAthway Database (SPAD) is an integrated database for genetic information and signal transduction systems. http://www.grt.kyushu-u.ac.jp/eny-doc/spad.html, downdloaded Feb. 23, 2004.

Chi et al., "A Spreadsheet Approch to Information Visualization", Proceedings of the 1997 IEEE Symposium on Information Visualization (InfoVis, 1997.

Dahiquist et al., "GenMAPP, a new tool for viewing and analyzing microarray data on biological pathways", nature genetics, vol. 31, May 2002.

Doniger et al., "MaPPFinder: Using Gene Ontology and GenMAPP to create a global gene-expression profile from microarray data", Genome Biology 2003, vol. 4, Issue 1, Article R7.

Wolf et al., "Case Study: Visualizing gene expression in its metabolic context", Henry Stewart Publications, 1467-5463, Briefings in Bioinformatics, vol. 1, No. 3, 297-304, Sep. 2000.

Ideker et al., Entitled "Integrated Genomic and Proteomic Analyses of a Systematically Perturbed Metabolic Network", Science, vol. 292, May 4, 2001.

Friedman et al., entitled "GENIES: a natural-language processing system for the extraction of molecular pathways form Journal articles,"bioinformatics, vol. 17, suppl. 1 2001, pp. S74B2.

S.B. Davidson et al. "K2/Kleisli and GUS Experiments in Integrated Access to Genomic Data Sources", IBM Systems Journal, vol. 40, No. 2, pp. 512-531. 2001.

Chung et al. Lleisli: a new tool for data integration in biology, Trends in Biotechnology vol. 17, pp. 351-355 (1999).

Timothy A. Howes, "The lightweight Directory Access Protocol: X.500 Lite", Citi Technical Report 95-8, University of Michigan, Jul. 27, 1995, pp. 1-9.

Benson, et al; "GenBank", Nucleic Acids Research, 1999, vol. 27, No. 1, Revised Oct. 5, 1998, Accepted Oct. 5, 1998, Abstract, pp. 38-43.

Benson, et al. "GenBank", Nucleic Acids Research, 2000, vol. 28, No. 1, Revised Oct. 4, 1999, Accepted Oct. 13, 1999, Abstract, pp. 15-18.

Fruitt, et al. "RefSeq and LocusLink: NCBI gene-centered resources", Nucleic Acids Research, 2001, vol. 29, No. 1, Received Oct. 2, 2000, Accepted Oct. 4, 2000, pp. 137-140.

Berman, et al. "The Protein Data Bank", Nucleic Acids Research, 2000, vol. 28, No. 1, Received Sep. 20, 1999, Revised and Accepted Oct. 17, 1999, pp. 235-242.

W. Yeong, "Lightweight Directory Access Protocol", Mar. 1995, www.jetf.org.rfc/rfc1777.txt pp. 1-22, no date.

P. Mockapetris, "Domain Names-Concepts and Faxilities", www.jetf.org.rfc/rfc1034.txt pp. 1-55, no date.

The Source for Java Technology JNDI ,, www.java.sun.com/search.java/jndi. 2 pages, web page, no date.

NCBI LocusLink, Introduction, www.ncbi.nlm.nih.gov/LocusLinks 2 pages, web page, no date.

GeneCards, www.bioinformatic.weizmann.ac.il/cards/ 2 pages, web page, no date.

NCBI, National Center for Biotechnology Information, www.ncbi.nlm.nih.gov/ 3 pages, web page, no date.

PPB "Protein Data Bank" www.rcsb.org/pdg/ 2 pages, web page, no date.

OMG, Object Management Group, www.omg.org/ 2 pages, web page, no date.

Karp et al., entitled "Integrated pathway/genome database and their role in a drug discovery", Trends in Biotechonology, 17(7):275-281, 1999.

Viecas, John, "Running Microsoft Access 97," Dec. 31, 1997, Microsoft Press, pp. 44, 46-47, 125-126, 146, 148-149, 194, 204-209, 211-215, 229-237, 257-259, 360-364, 448-449, 584, 586-588, and 609.

Website: http://ncbi.nlm.nih.gov/Locustlink, entitled "LocusLink Introduction," dated May 22, 2002.

Website: http://www.gdss.com/wp/IBIS.htm, entitled "The IBIS Manual A Short Course in IBIS Methodology," GDSS working papers dated May 7, 2002.

Website: http://www.bind.ca/index.phtml?page=Databases, entitled "BIND-The Biomolecular Interaction Network Database", May 22, 2002.

Website: http://www.grt.kyushu-u.ac.jp/spad, SPAD: Signaling Pathway Databases. "The Signaling Pathway Database (SPAD) in an integrated database for genetic information and signal transduction system" May 22, 2002.

Website: http://www.transpath.gbf.de/, Transpath Signal Transduction Browser, Transpath Home Pages May 22, 2002.

Website: http://www.transfac.gbf.de/TRANSFAC/, entitled TRANSFAC- The Transcription Factor Database May 22, 2002.

Website: http://www.kegg.com—KEGG: Kyoto Encyclopedia of Genes and Genomes- May 22, 2002.

Website: http://www.uspto.gov/patht. United States Patent and Trademark Office Patent Full-Text and Full-page Image Database May 22, 2002.

Website: http://www.ncbi.nlm.nih.gov/omin National Center for Biotechnology Information- OMIM: Online Mendelian Inheritance in Man-Home page, May 22, 2002.

Website: http://www.ncbi.nlm.nih.gov/entrez/quer.fcgi. NCBI, National Library of Medicine, PubMed, May 22, 2002.

Website: http://www.citeseer.nj.nec.com/cs, NEC ResearchIndex, May 22, 2002.

Website: http://www.google.com. GOOGLE dated May 22, 2002.

Website: http://ecocyc.com, entiled "EcoCyc: Encyclopedia of *Eserichia coli* Genes and Metabolism", dated May 22, 2002.

Website: http://www.sigenetics.com, entiled "Silicon Genetics, GeneSpring4.2," dated Feb. 21, 2002.

Website: http://biocyc.org/ecoli/, entitled "EcoCyc: Encyclopedia of *Eserichia coli* Genes and Metabolism", BioCyc knowledge library, dated May 22, 2002.

Website: http://www.empproject.co, entitled "EMP Project", dated May 22, 2002.

Website: http://www.silicongenetics.com/cgi/Sig.cgi/Products/GeneSpring/index.smf/, entitled Silicon Genetics: gene Expression software, May 21, 2002.

Website: http://www.bioinformatics.weizmann.ac.il/cards/, entitled "GeneCards Homepage", dated May 22, 2002.

Website: http://www.ncbi.nlm.nih.gov/Sitemap/, entitled "NCBI Site Map: Guide to NCBI Resources", dated May 22, 2002.

Website: http://genome.ucsd.edu, entitled "Bioinformatics and Computational Biology Home Page", dated May 22, 2002.

\* cited by examiner

SYSTEMS, METHODS AND COMPUTER READABLE MEDIA FOR PERFORMING A DOMAIN-SPECIFIC METASEARCH, AND VISUALIZING SEARCH RESULTS THEREFROM

CROSS-REFERENCE

This application is a continuation-in-part application of application Ser. No. 10/033,823, U.S. Pat. No. 6,920,448, filed Dec. 19, 2001; and is a continuation-in-part of application Ser. No. 10/155,304, U.S. Pat. No. 7,058,643, filed May 22, 2002, and is a continuation-in-part of application Ser. No. 10/642,376, U.S. Pat. No. 7,228,302, filed Aug. 14, 2003, and is a continuation-in-part of application Ser. No. 10/641,492 filed Aug. 14, 2003, pending; and is a continuation-in-part of application Ser. No. 10/154,524 filed May 22, 2002, pending; and is a continuation-in-part of application Ser. No. 10/154,529, U.S. Pat. No. 7,155,453, filed May 22, 2002, and is a continuation-in-part of application Ser. No. 10/155,616 filed May 22, 2002, pending; and is a continuation-in-part of application Ser. No. 10/784,523 filed Feb. 23, 2004, pending; and is a continuation-in-part of application Ser. No. 10/155,405, abandoned, filed May 22, 2002, which is a continuation-in-part application of application Ser. No. 09/863,115, abandoned, filed May 22, 2001. This application also claims the benefit of U.S. Provisional Application No. 60/289,927, filed May 9, 2001. Each of application Ser. Nos. 10/033,823; 10/155,304; 10/642,376; 10/641,492; 10/154,524; 10/154,529; 10/155,616; 10/784,523; 10/155,405; 09/863,115; and 60/289,927 is hereby incorporated herein, in its entirety, by reference thereto.

BACKGROUND OF THE INVENTION

With the rapid growth of the internet and users of the internet over the recent years, a concomitantly rapid increase in the amount of information available over the internet has developed. While, at first blush, this explosion in information available to the user would seem a welcome asset, it carries along with it several downside aspects to the user, not the least of which are the ever increasing difficulties in sorting through the vast quantities of available information to find those information sources which are most pertinent to the search at hand.

Many search engines, such as Google™ and AltaVista®, for example, are available to users and provide powerful search tools for general use. These search engines enable any user to query the vast repository of public web-based documents that are indexed by these systems. However, the sheer volume of available data causes an undesirable result in many of these general searches as most simple searches return large and unmanageable volumes of hits or results, many of which are not useful or relevant to that which the user is seeking.

Most of the available search engines employ different strategies from one another in attempting to find matches to information which is most relevant to the user-supplied search criteria. Therefore, each search strategy imposes its own bias with regard to the relevancy of documents that are retrieved, and one search engine may provide superior results for any given search, while another search engine may provide superior search results for a second, different search. For example, a search engine may determine the relevance of a document by the number of "hits" or matches of any of the key words in the user-supplied query to actual occurrences of those words (or other search terms) in the document. However, the mere repetition of a relevant term is no guarantee that the document is relevant, and often the content of a document identified in this way has little or no relevance to the subject of interest to the user. This results in great expenditures of time, as the user must open documents which are indicated to be relevant, and read them to make a determination as to whether they are in fact relevant, in effect requiring a great deal of "manual searching" by the user to get to the documents actually needed.

Further, different search engines often set different priorities as to which sites to index, and therefore collect disparate results with regard to the same user-supplied query, even prior to making any relevancy assignments.

Another way of attempting to retrieve relevant documents is by filtering, wherein an interface is provided to allow the user to set parameters to arrive at a set of relevant terms. In this way, the user manually determines which items in a set of relevant items delivered are the most relevant. This approach has the potential of eliminating some of the time required to cull through non-relevant documents that might have otherwise been provided by the previous approach discussed. However, time is still required for manual settings. Additionally, the manual settings may potentially eliminate relevant documents which would have otherwise been presented by the previously described approach.

Metasearch engines are available (for example, metacrawler®, Dogpile®, Search.com, etc) which act as a "middleman" between the user and a number of search engines of the types described above. In this way, a user can submit a single query to a metasearch engine, and the metasearch engine then parses and reformats the query. The reformatted queries are then forwarded to numerous search engines, such as those described above, with each discrete search engine receiving an appropriately formatted query pursuant to the protocols for that search engine. After retrieving the results from the individual search engines, the metasearch engine presents them to the user. Aside from the simplification provided to the user in having to format only one query, a goal of this approach is that by forming a composite of results, relevant documents that may have been missed by any one search engine employed will be found and retrieved by another.

Although these metasearch engines simplify the query task by the user and are thus somewhat useful and provide a measure of time savings, they do nothing to try and categorize or otherwise make sense of the results to make them more quickly accessible. As such, the user is usually left with a very large set of raw results (relatively unordered documents) to examine. Further, these metasearch engines search generic indexes such as Google™ (permission and/or license may be required for metasearching on Google™) or AltaVista® and do not include sites of specific relevance to the sciences.

Current web-based search engines that employ data mining capabilities include northernlight.com, huskysearch and vivisimo. These systems generally employ some type of unsupervised clustering to group documents by similar topics. These systems are an improvement over the generic metasearch engines described above in that the user can see the search results provided in clusters or sub-groups and can then potentially eliminate clusters or sub-groups which appear to have low relevance value and/or can more quickly access those documents in sub-groups which appear highly relevant. In none of these examples, however, have data mining algorithms been tuned specifically to the sciences, or more particularly, the life sciences. Thus, common scientific terminology which has no real discrimination value in a scientific search will be over-weighted, when using these types of systems, as being significant when it is not. Although it is possible to retrieve relevant information to a scientific search using the above generic types of search engines and data mining tools, it is also likely that many relevant documents will not be found, since access to specialized sites (such as PubMed, SwissProt, Entrez, EMBL, etc, in the case of a life sciences search) is not directed.

Attempts at providing domain-specific implementation of metasearch tools have been made which include searchlight-.cdlib.org, researchville.com, bio-crawler, gateway.nlm.nih-.gov and queryseverver.com. Searchlight provides a few scientifically focused metasearches but has no clustering capability. researchville.com provides a medically oriented implementation, but also lacks any clustering capability. bio-crawler appears to provide biology specific searches in Japanese, but again with no clustering capability. gateway.nlm.nih provides access to various government databases, including medical databases, but also lacks any clustering capability. queryserver.com provides health-oriented metasearches with clustering of results, but is a server-based tool and does not provide the capability of combining both generic and domain specific searches, nor is categorization performed. Being server-based, its configuration is determined by the server administrator and therefore lacks the potential for end-user customization.

Various client-based solutions for searching have also been proposed. webferret.com provides a simple to use client application that provides metasearch capabilities, but it provides no data mining capabilities and is restricted to a fixed list of generic search engines. DynaCat and QueryCat (http://www.ics.uci.edu/~pratt/) are applications that use a client tool to query domain-specific information within MedLine. These tools are not metasearch engines and thus do not have the capability of querying multiple search engines.

It would be desirable to have domain-specific tools for efficiently performing scientific metasearches and for organizing the results of such searches to enable the user to quickly identify and access the most relevant information discovered.

SUMMARY OF THE INVENTION

Method, systems and computer readable media for performing a domain-specific metasearch, and obtaining search results therefrom are provided. A metasearch engine capable of accessing generic, web-based search engines and domain-relevant search engines is configured to receive one or more queries inputted by a user, and to search for documents on at least one of the generic, web-based search engines and domain-relevant search engines which are relevant to the queries. Raw data search results are fetched in the form of text documents from each of the at least one generic, web-based search engines and domain-relevant search engines. Relevant data including semantic information is extracted from the raw data search results and converted to a local format. The relevant data having been converted to the local format may then. be visualized as a network visualization.

A system for performing a domain-specific metasearch, and obtaining search results therefrom, is provided, including: a metasearch engine capable of accessing generic, web-based search engines and domain-relevant search engines, wherein upon receiving one or more queries inputted by a user, the metasearch engine searches for documents on at least one of the generic, web-based search engines and domain-relevant search engines which are relevant to the queries, and fetches raw data search results in the form of text documents from each of the at least one generic, web-based search engines and domain-relevant search engines; a local format module configured to extract relevant data including semantic information from the raw data search results and convert the relevant data, including the semantic information, to a local format; and a user interface configured to visualize the relevant data having been converted to the local format as a network visualization.

Methods, systems and computer readable media for performing a domain-specific metasearch, and obtaining search results therefrom are provided in which a metasearch engine capable of accessing generic, web-based search engines and domain-relevant search engines is provided to receive one or more queries inputted by a user to the metasearch engine and searching for documents on a selected set of the generic, web-based search engines and domain-relevant search engines which are relevant to the queries. Raw data search results are fetched in the form of text documents from each member of the selected set, and relevant data including semantic information is extracted therefrom. The relevant data including semantic information is converted from raw results to a local format and linked with a pre-existing, locally formatted data set which matches the relevant data. At least one of ranking and filtering may be preformed on the raw data search results based on the linking the relevant data to the pre-existing data. The results of the ranking and/or filtering of the raw data may then be visualized.

Methods, systems and computer readable media are provided for performing a domain-specific metasearch, and obtaining search results therefrom, in which a metasearch engine capable of accessing generic, web-based search engines and domain-relevant search engines is provided. One or more queries inputted by a user to the metasearch engine are received and documents are searched for, based on a selected set of the generic, web-based search engines and domain-relevant search engines which are relevant to the queries. Raw data search results are fetched in the form of text documents from each member of the selected set, and relevant data including semantic information are extracted from the raw data search results and converted to a local format. The relevant data in the local format may be linked with a pre-existing, locally formatted data set which matches the relevant data, and the linked relevant data and pre-existing, locally formatted data that matches, may be visualized as a network visualization.

These and other advantages and features of the invention will become apparent to those persons skilled in the art upon reading the details of the systems, methods and computer readable media as more fully described below.

DETAILED DESCRIPTION OF THE INVENTION

Figure 1:
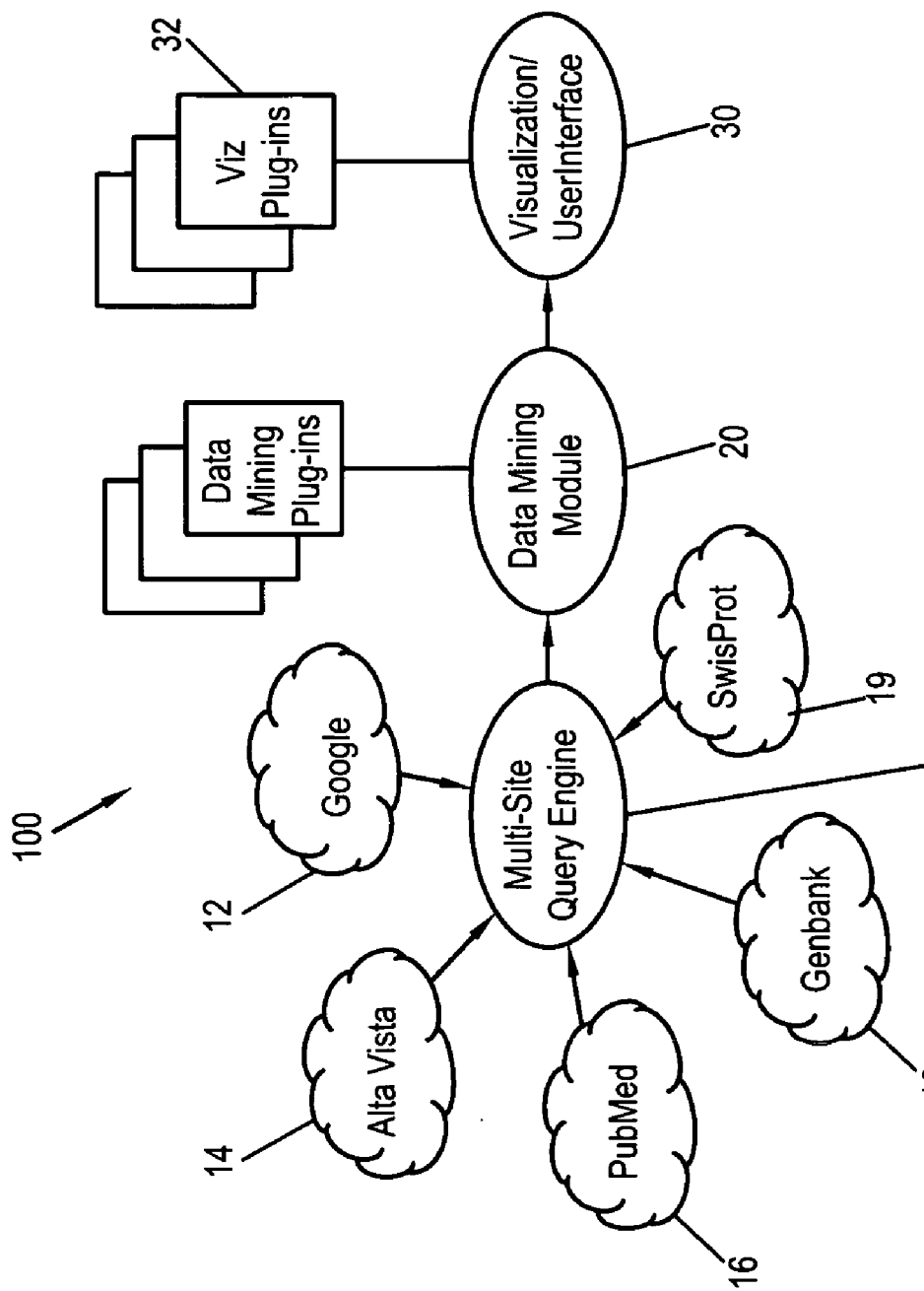
FIG. 1 is an architectural schematic of a system according to the present invention.

Before the present systems and methods are described, it is to be understood that this invention is not limited to particular hardware or software described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and systems similar or equivalent to those described herein can be used in the practice or testing of the present invention, the preferred methods and systems are now described. All publications mentioned herein are incorporated herein by reference to disclose and describe the methods and/or systems in connection with which the publications are cited.

It must be noted that as used herein and in the appended claims, the singular forms "a", "and", and "the" include plural referents unless the context clearly dictates otherwise. Thus, for example, reference to "a node" includes a plurality of such nodes and reference to "the interaction" includes reference to one or more interactions and equivalents thereof known to those skilled in the art, and so forth.

The publications discussed herein are provided solely for their disclosure prior to the filing date of the present application. Nothing herein is to be construed as an admission that the present invention is not entitled to antedate such publication by virtue of prior invention. Further, the dates of publication provided may be different from the actual publication dates which may need to be independently confirmed.

DEFINITIONS

The term "hit" may be referred to a document that is selected through a search technique by matching a query term with a term existing in that document. Alternatively, when referring to a single document, a number of "hits" may be counted as each individual match of a query term within that document.

The term "URL" is an acronym for "uniform resource locator", which designates the "address" or location of a document, Web site or other information on the world wide web.

The term "user" refers to an agent, human, computer or other mechanism capable of providing a query and of receiving search results.

The term "query" refers to the information that is sent to the metasearch engine to define the subject matter that the user is interested in searching.

The term "biological diagram", "network diagram" or "biological model", as used herein, refers to any graphical image, stored in any type of format (e.g., GIF, JPG, TIFF, BMP, etc.) which contains depictions of concepts found in biology. Biological diagrams include, but are not limited to, pathway diagrams, cellular networks, signal transduction pathways, regulatory pathways, metabolic pathways, protein-protein interactions, interactions between molecules, compounds, or drugs, and the like.

A "biological concept" refers to any concept from the biological domain that can be described using one or more "nouns" according to the techniques described herein.

An "entity" or "item" is defined herein as a subject of interest that a researcher is endeavoring to learn more about, and may also be referred to as a biological concept, i.e., "entities" are a subset of "concepts". For example, an entity or item may be one or more genes, proteins, molecules, ligands, diseases, drugs or other compounds, textual or other semantic description of the foregoing, or combinations of any or all of the foregoing, but is not limited to these specific examples.

An "interaction" as used herein, refers to some association relating two or more entities. Co-occurrence of entities in an interaction implies that there exists some relationship between those entities. Entities may play a number of roles within an interaction. The structure of roles in an interaction determines the nature of the relationship(s) amongst the various entities that fill those roles. An empty role in an interaction can be referred to as a "slot" or placeholder, where an entity may be assigned.

When one item is indicated as being "remote" from another, this is referenced that the two items are at least in different buildings, and may be at least one mile, ten miles, or at least one hundred miles apart.

"Communicating" information references transmitting the data representing that information as electrical signals over a suitable communication channel (for example, a private or public network). "Forwarding" an item refers to any means of getting that item from one location to the next, whether by physically transporting that item or otherwise (where that is possible) and includes, at least in the case of data, physically transporting a medium carrying the data or communicating the data.

A "processor" references any hardware and/or software combination which will perform the functions required of it. For example, any processor herein may be a programmable digital microprocessor such as available in the form of a mainframe, server, or personal computer (desktop or portable). Where the processor is programmable, suitable programming can be communicated from a remote location to the processor, or previously saved in a computer program product (such as a portable or fixed computer readable storage medium, whether magnetic, optical or solid state device based). For example, a magnetic or optical disk may carry the programming, and can be read by a suitable disk reader communicating with each processor at its corresponding station.

"May" means optionally.

Methods recited herein may be carried out in any order of the recited events which is logically possible, as well as the recited order of events.

"Local format" refers to a restricted grammar/language used to represent extracted semantic information from diagrams, text, experimental data, etc., so that all of the extracted information is in the same format and may be easily exchanged and used in together. The local format can be used to link information from diverse categories, and this may be carried out automatically. The information that results in the local format can then be used as a precursor for application tools provided to compare experimental data with existing textual data and biological models, as well as with any textual data or biological models that the user may supply, for example.

A "node" as used herein, refers to an entity, which also may be referred to as a "noun" (in a local format, for example). Thus, when data is converted to a local format according to the present invention, nodes are selected as the "nouns" for the local format to build a grammar, language or Boolean logic.

A "link" as used herein, refers to a relationship or action that occurs between entities or nodes (nouns) and may also be referred to as a "verb" (in a local format, for example). Verbs are identified for use in the local format to construct a grammar, language or Boolean logic. Examples of verbs, but not limited to these, include up-regulation, down-regulation, inhibition, promotion, bind, cleave and status of genes, protein-protein interactions, drug actions and reactions, etc.

Referring to FIG. 1, an architectural schematic of a system for performing searches and data mining according to the present invention is shown. A metasearch (multi-site query) engine 10 is provided with the capability of using multiple search engines to find appropriate web documents for processing. Search terms and requested number of hits may be inputted by the user and are used to construct a query URL string for each search engine. The particular URL's are then invoked via http and returned pages are processed to extract the individual search results.

A variety of repositories may be searched including not only standard web-based sites which are accessible by search engines 12 and 14 (such as Google™ (permission and/or license may be required for metasearching on Google™) and Altavista®, for example, although many other generic search engines can be used) but also publication sites including, but not limited to sites such as PubMed 16, GenBank 18, OMIM and others, sequence databases, protein structure databases such as PDB, for example, pathway information databases such as EMP, for example and other data specific sites. Even similar sorts of engines, such as the generic search engines, have different priorities about what sites they search and therefore the present invention is capable of using numerous engines for not only generic sites, but publication sites, and other domain-specific sites. For example, similar engines cycle through different portions of the web to update the site. Different search engines are likely to be in different time lines of where they are updating their indexing, therefore, a more up to date, overall search can be achieved by employing more than one engine for each type of site search.

Similarly, sequence sites and other data specific sites, including, but not limited to sites such as SwissProt 19, Entrez Nucleotide, Entrez Protein, EMBL and PDB may be accessed. Random databases, including those accessible over the world wide web and privately owned or other databases available internally over an intranet may also be accessed. Those databases which are not in a format that can be displayed as web pages can be interfaced with a web interface that enables search results of such a database to be displayed in the form of web pages. For example, in the case of an in house Java application talking to a relational database, a web interface can be constructed so that the present search system can interface with the relational database and obtain results in the form of web pages. It is noted that most bioinformatics databases already have web interfaces available.

The sites given in the example of FIG. 1 that are accessible by system 100 are highly relevant to molecular biology and the life sciences and therefore dramatically improve the domain-specific relevance of search hits in comparison to using standard publicly available search engines. Other content-specific publication sites and databases which are specific to other scientific fields can be constructed similarly for domain-specific searches.

An important aspect of the search features of the present invention is its use of text-based data as a data normalization technique. Using this approach, any data that can be reduced to a query returning a web-based text document can be incorporated into the system. Thus, genome and protein sequence data may be included as part of the metasearch, as well as more traditional publication documents. In principle, any system, including in-house proprietary databases, can be wrapped in a CGI(common gateway interface)-based web application server so that its data is also included in a metasearch performed according to the present invention.

Figure 2:
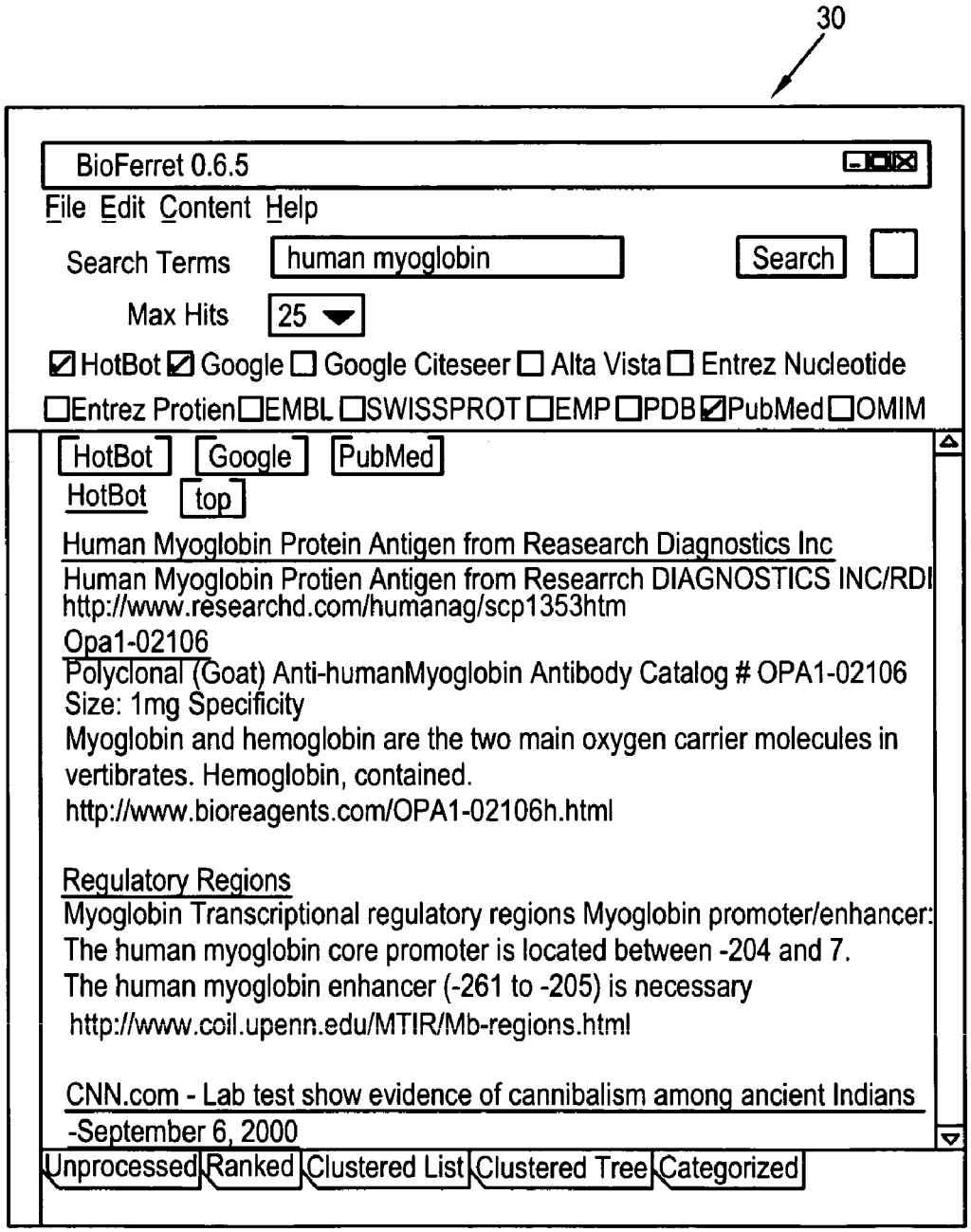
FIG. 2 shows an example of a screen display on a user interface which is displaying the initial raw results of a search conducted.

A list of sites available for searching may be provided to the user at the user interface 30, and may be displayed in a visual/graphical manner, such as shown in FIG. 2, for example. In this example, the sites available for searching each have a box provided adjacent thereto which may be checked by a user (using a mouse or keyboard to selectively check the box) to select each particular site to be searched. The boxes can also be unchecked in the same manner to deselect a site. In this way the user can easily customize a search by selecting only those sites desired.

Additionally, a "context" menu may be provided that allows selections of "presets" of groups of search engines. For example, the "Publication" context may select Citeseer, PubMed and OMIM, as these are all publication oriented sites and may be grouped together as such. The Context menu may also be configured to group presets relating to other scientific fields as well, for example, a "Publication-Physics" context may include Physics specific publication sites. Similarly, a "Sequence" context may be included in the context menu to allow a selection of a group of sequence sites, such as Entrez Nucleotide, Entrez Protein, EMBL, SwissProt and PDB, for example.

The lists of sites to be searched can be easily extended to include additional sites, as an open architecture is provided to allow addition and deletion from the list through the use of plug-ins or other programming modification. Alternatively a centralized repository can be provided in XML language, for example, which can be fetched through the internet or local intranet each time a user links up with the system, or upgrades could periodically be made available through the same channels.

Once the query has been formulated, the search sites have been selected, and the query has been submitted to multi-site query engine 10, engine 10 interrogates the identified generic, web-based search engines and other identified sites with the user-supplied query terms of the query. The results from each engine/site 12,14,16,18,19 are retrieved and parsed to extract the search hits for use later in the process. The search hits are data that are returned from the various search engines, with each containing a URL, title and usually some brief descriptive language. The present invention constructs counterparts to these for data returned from sequence data sites and other domain-specific sites which do not already provide this standard format for a hit. The search hits are combined into an HTML document showing the combined search results. The source document corresponding to each search result is then explicitly fetched and a collection of text documents is created which represents the results of the overall search.

The document data may be immediately displayed at visualization/user interface 30, and, at the same time, data mining module 20 begins processing the document data. FIG. 2 shows an example of a screen display on user interface 30 which is displaying the initial raw results of a search conducted using a system according to the present invention. In this example, the following sites were selected for searching: HotBot, Google, and PubMed. The query that was executed was for "human myoglobin". FIG. 2 shows raw results obtained from the HotBot search engine. The results may be listed as a title of a document in HTML format such that the document may be directly accessed by the user clicking on the underlined title with a mouse interface or by entering a selection through a keyboard connected with the system. A brief description of the document follows the title and the description is followed by the URL (uniform resource locator) address of the document. The documents may be grouped according to each search engine that is being used and may appear with predefined relevance rankings, if any, according to schemes used by that particular search engine. That is, the results may initially be listed in the order that they appear with regard to each particular search engine. In some cases, like Google, the results may be listed in an order corresponding to some scheme for relevancy ranking. In other cases, like for sequence databases, the results may be presented merely by the order in which the hits were identified or located, or by alphabetical order. Whatever the case, the present invention does not attempt to interpret the order in which the results are displayed at this stage of processing.

The raw results may be displayed immediately upon retrieval, at the same time that they are supplied to the data mining module for further processing, so that the user may begin browsing the raw results at the same time that data mining processing is being carried out. This provides the user the opportunity of manually identifying one or more highly relevant documents even as further processing is carried out, which may save the user time in such an event.

In reviewing the list of raw data from HotBot in FIG. 2, it can be seen that three of the documents shown relate to cannibalism in the $12^{th}$ Century Southwest by Anasazi Indians. Although this information could be highly relevant for a specific search regarding cannibalism, it is not likely to be relevant to many scientific searches relating to technical details of human myoglobin. As such, this is a good example of how generic databases and search engines can return documents marked "highly relevant" which are really not relevant at all to a specific scientific inquiry.

Processing by data mining module 20 processes the raw data to prepare a single list of documents from all of the sites searched, wherein the documents are ranked by simple relevance scores. In preparing this list, data mining module 20 fetches URL's individually for data mining. All items/documents that were not reachable via the web, either due to networking problems or because the page no longer exists are removed from the list. Further, data mining module 20 strips off all HTML text formatting.

Figure 3:
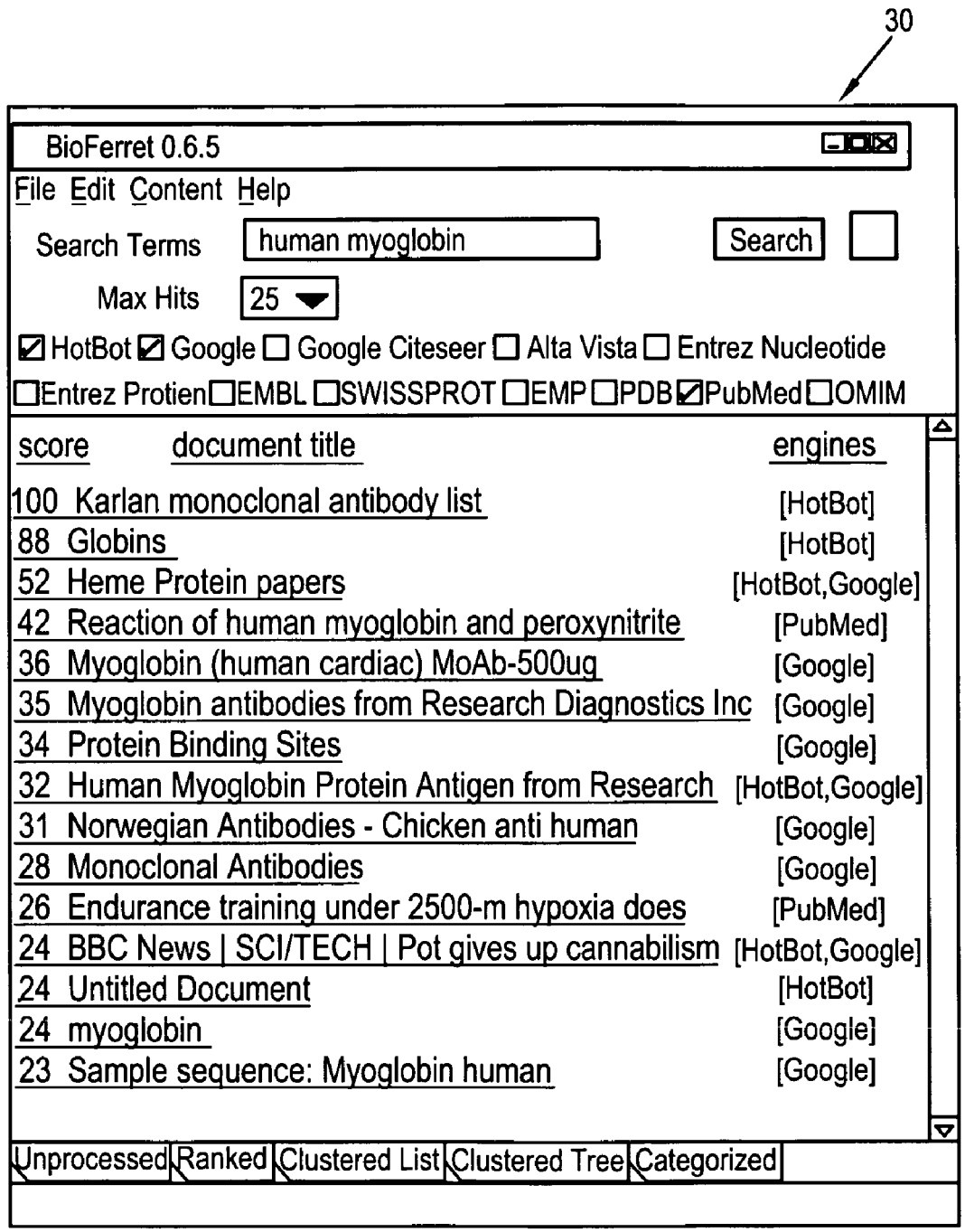
FIG. 3 shows an example of a screen display on a user interface which is displaying document search results according to simple relevance ranking.

A simple relevance ranking may then be generated based upon the frequency of the search terms that are found within any particular document (e.g., a total number of "hits" of search terms within a document is tallied. A weighting function may also be applied to hits that occur in a title, for example, or other likely more relevant location, such as an abstract). The raw relevance scores may then be normalized to a scale of 1 to 100 and the documents are listed according to decreasing relevance scores. A display of document search results according to simple relevance ranking on user interface 30 is shown in FIG. 3.

As noted above, the first procedure in the data mining process is to remove documents having "dead" or invalid URL entries from the list of results. Duplicate entries are also removed at this time. As can be seen in FIG. 3, a double occurrence of the document "ABQjournal" has been compressed to a single occurrence on the list of results. The fact that this entry had a double occurrence is evidenced by the listing of HotBot twice under the "Engine" column. A simple relevance score may also be computed for the display at this stage of processing (shown under the "Score" column in FIG. 3) and the search results are listed in descending order according to their simple relevance score.

The simple relevance score may be computed as follows: for each document, the number of times each search term is found is counted and tabulated. For example, with regard to the search for "human myoglobin", if there are three occurrences of "human" in a particular document and five occurrence of "myoglobin", then that document receives an initial score of eight. Next, the title of the document, as constructed by the results parser of the present invention (as opposed to the official HTML title) is parsed for the same search terms. Each occurrence in the title counts for a weighted value (a value of ten, for example, although weighting can certainly be varied to take on some other value), since it is expected that when a search term appears in the title there is a higher probability that the document will be relevant to the search. So, to follow with the example, if the document described contained one occurrence of "myoglobin", the total score for the document would be eighteen (8+10). The scores for each document may then be normalized so that the maximum score for the total search is "100" and so that scores range from "0" to "100". Normalization is accomplished by simply finding the maximum score and then multiply each score by (100/maximum score).

The relevance scoring technique provided above is just one example of simply calculating statistics against the identified documents as a way of "predicting" relevancy to the information that the searcher desires. Any number of various statistical and/or weighting schemes could be employed in this process and the present invention is not to be limited to the specific example provided. Further multiple metrics may be used to provide more than one way of ranking for relevancy and then the user can be provided the opportunity to sort the document results by choosing whichever metric thought to be best suited for the particular search. Of course, the first metric chosen need not be solely relied upon, but could be compared with others by selecting and sorting according to another metric.

Another function that may be carried out by the data mining module involves the clustering of similar documents together in groups or clusters. A wide search which searched disparate sites/databases as described herein can give results that a user wouldn't expect to find, such as the "cannibalism" documents identified herein when searching "human myoglobin". In such a situation, clustering can be an effective way of sorting such documents together in a group, so that they can be dealt with simultaneously. A simple document clustering procedure may be performed, during which documents are grouped or clustered based on unsupervised clustering, wherein documents are grouped according to similarity of content without any other intervention. At a high level, a similarity measure is first defined to assess how similar a pair of documents are. An example of a similarity measure is the proximity score "$S_{ij}$" (defined below) although other algorithms can be substituted for use as a similarity measure.

Custom stop word lists may also be provided which are tailored to the specific site that is being searched. An example of this would be to include the word "sequence" as a stop word for the custom stop word list used in searching a sequence database, as this word is used ubiquitously in such a database and has relatively little discrimination value, since it is already known that all, or substantially all of the documents to be searched in such a database pertain to sequences. On the other hand, the word "sequence" may have significant discriminatory value when searching a generic site and thus would not be included in the custom stop word list referred to when searching Google™, for example.

The present invention may automatically generate stop word lists customized to each site by identifying site specific stop words and removing these words from the documents in respective sites before clustering the documents or other additional or alternative processing as described herein. One technique for such automatic generation involves preparing a list of words, specific to each site, wherein each word in the list is a word that is contained in all documents found at that particular site. The underlying assumption for concluding that such words are stop words for that site, is that they have no discriminatory value to that site, since all (or at least a large percentage) of the documents retrieved from that site contain those particular words. Many times these words will appear in the headings or links on the site of the search engine. Since these words may change as the search engine site is modified, or even for different searches performed on the same unmodified site, an automatic preparation of the stop words, created "on the fly" for each query may be provided for better tailoring of results. These stop words are used to filter out site-specific words and words with low discrimination value from documents retrieved from each search engine site. The terms (after having removed the stop words) present in a document may then be used to compute the proximity scores between the documents.

Once the similarity measure has been defined, a number of different techniques may be used to cluster the documents (e.g., partitional clustering, hierarchical clustering, etc.). In one example, a technique referred to as group-average-linkage hierarchical clustering is performed. According to this technique, each document is first placed into an individual cluster, so that the total number of initial clusters equals the total number of documents. A comparison is then made on a cluster-to-cluster basis, using a similarity measure (such as a proximity score, for example), to determine which clusters are the most similar, as determined by the highest similarity or proximity score. Once two clusters have been combined into a single cluster (as in forming a cluster having two documents in the first round of the procedure) the similarity or proximity scores of every other cluster are recomputed with respect to the newly created cluster using the group average similarity or proximity score. It is noted that with each "round" or "step", a new cluster is created from two previously existing clusters having the highest similarity or proximity score with respect to one another. Thus, for example, if cluster "i" is combined with cluster "j" in the current round to form cluster "k", then during recomputation of proximity scores, the proximity score between pre-existing cluster "l" and newly formed cluster "k" is determined by computing the average of the proximity score of cluster "i" to cluster "l" and cluster "j" to cluster "l", and weighed by the number of terms in cluster "i" and cluster "j". The clustering process continues round by round until a stop condition is reached, which may be a predetermined proximity score limit, a predefined number of final clusters, or the like.

An algorithm that can be used by the data mining module for the clustering procedure according to the above-described group-average-linkage technique is described hereafter. A proximity score $S_{ij}$ representing the distance between two documents "i" and "j" can be computed as follows:

$$S_{ij} = 2 \times (\tfrac{1}{2} - N(T_i, T_j)/(N(T_i) + N(T_j)));$$

Where $T_i$ is a term in document i;

$T_j$ is a term in document j;

$N(T_i, T_j)$ is the number of co-occurring terms that documents i and j have in common;

$N(T_i)$ is the number of terms found in document I; and $N(T_j)$ is the number of terms in document j.

By normalizing the scores as described above, identical documents (i.e., two documents having all terms in common) will have a proximity distance of zero (0), while completely orthogonal documents (i.e., having no terms in common) will have a proximity score of one (1). The hierarchical clustering procedure may be run until all the documents fall into one cluster. In order to view the results of the hierarchical clustering, a stop point can be set by the user to display the status of the results of the hierarchical clustering at any round or step intermediate of the processing, i.e., after beginning the clustering process, but before all documents have been subsumed into a single cluster. Thus, a stop point can be set for a pre-set number of clusters, or when the proximity scores become greater than or equal to some pre-defined value between zero and one. Combinations of stop points can be set, such that display of clusters occurs whenever the first stop point is reached.

Figure 4:
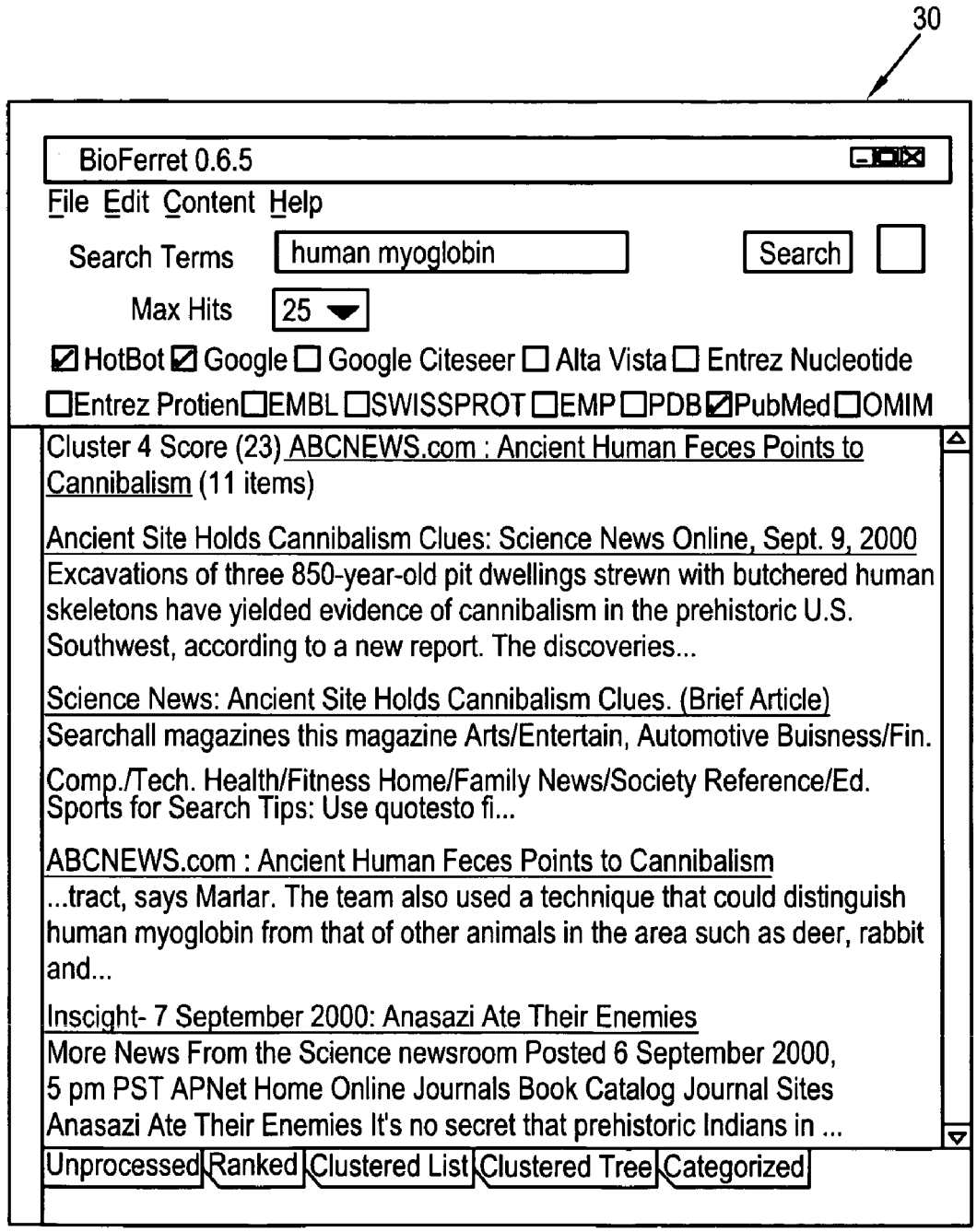
FIG. 4 shows an example of a screen display on a user interface which is displaying an example of a cluster formed.

An example of a cluster is displayed in FIG. 4 on user interface 30. In this example, Cluster 4 identifies a group of similar documents identified in the "human myoglobin" search described above, all of which relate to finding the substance in archeological digs that indicate that the Anasazi Indians may have practiced cannibalism. By clustering these documents about this particular topic, all of the documents relating to cannibalism in the Anasazi tribe can be examined together, and, if not particularly relevant, can be efficiently eliminated from further browsing. On the other hand, if this topic is of interest, all documents relating to the topic are conveniently grouped for retrieval and browsing without having to browse the rest of the data.

Figure 5:
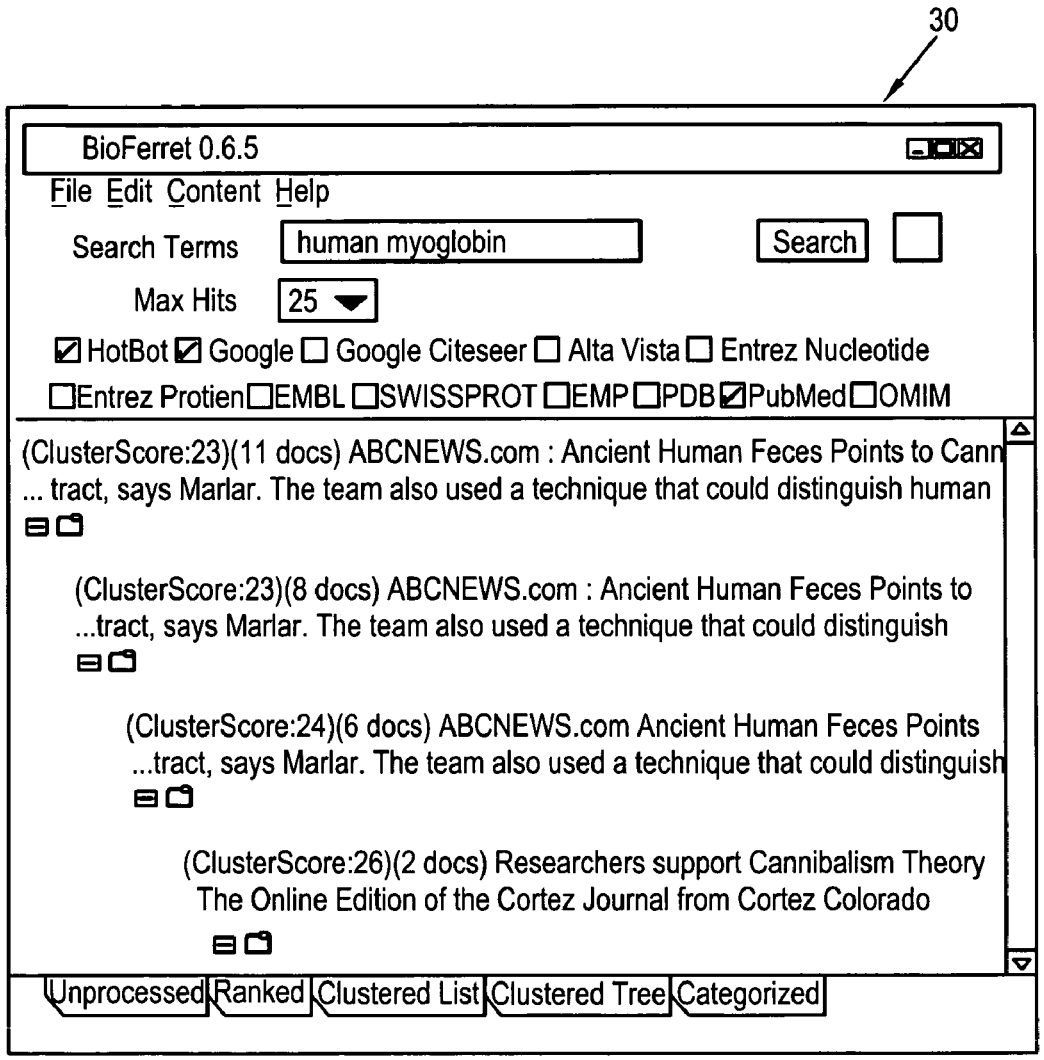
FIG. 5 shows an example of a screen display on a user interface which is displaying the same cluster identified in FIG. 4, but in a tree hierarchy format.

FIG. 5 shows the same cluster identified in FIG. 4, but displayed in tree hierarchy. The tree hierarchy form of display allows the user to delve deeper into clusters to see which documents are most closely related within a cluster. Whereas the "list" view of clusters shown in FIG. 4 represents an arbitrary cut-off as to where to define the cluster, by navigating the tree structure (FIG. 5) of the underlying cluster hierarchy, no such cut-off needs to be made. With appropriate data displayed on the user interface, the user can then determine which documents are closely related and which are not. The downside of the tree hierarchy is that it can be more tedious to navigate which can in some ways compound the problems inherent in navigating a larger number of search results. However, this view does give the user another option and sometimes will be more advantageous than using the list format.

A document classifier function may also be included such that the data mining module 20 classifies the documents according to predefined categories such as "Publications", "News", "Product Information", "Sequences" and "Miscellaneous", etc. According to this classification scheme, data mining module 20 consults a list of words for each category, with the lists containing words that are particular to the category being examined. The lists of words which are specific for each category may be either manually generated or automatically extracted, with the words in each list being particular to the respective category for which it is used. The automatic generation may be performed using a training set of documents which have been categorized, such that each document has a known category. A list of words that are the most discriminatory among the predefined categories is then identified from the training set, with regard to each category, and an automated procedure selects the lists of words automatically from the training set. The words which are "most discriminatory" are those which are identified by their occurring most often in one category as compared to low occurrences in other categories. The learning of the lists of words can be performed incrementally, by selecting the previous list of words for a given category, the categorization resulting therefrom and user feedback regarding the accuracy of categorization of a set of documents, to generate the list of discriminatory words for each category, respectively.

A score may be computed for each raw document to belong to a specific category based on the frequency of occurrence of each word in the word list of the specified category. The document is categorized into the category receiving the maximum score. If the number of unique words in the document matching those present in the list for the category getting the maximum score is less than a threshold (category-specific threshold, which may be user specified) then the document is classified into the Miscellaneous category. The order in which the categorization proceeds is not critical. In the example provided above, all of the documents relating to cannibalism were "News" stories and were grouped together as "News" by the categorization algorithm.

Figure 6:
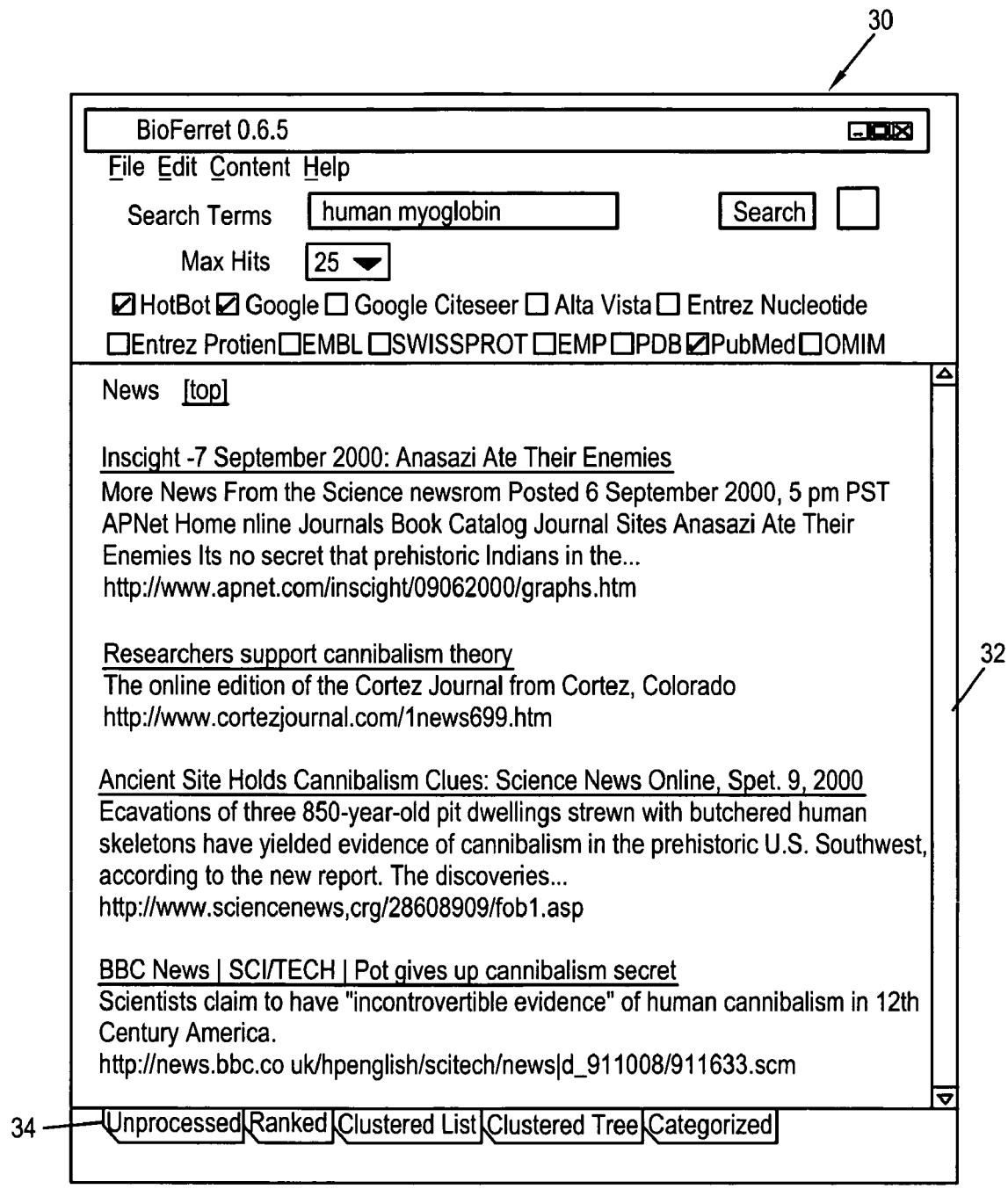
FIG. 6 shows an example of a screen display on a user interface which is displaying search documents according to categories.

FIG. 6 shows a screen display on user interface 30 that lists the search documents according to categories. Although only documents which are grouped in the "News" category" are shown in FIG. 6, the user would be able to readily access the other categories of documents (e.g., "Publications", "Product Information", "Sequences" and "Miscellaneous", by scrolling upwardly or downwardly with the side scroll bar 32.

After having performed the data mining procedures for simple relevance ranking, clustering (list and tree) and categorization as described above, the results of the differing organizational views of the data prepared by these data mining procedures may then be displayed on the user interface 30 upon selection of the corresponding button from button bar 34 (see FIGS. 2-6). Thus, a user is able to select search results to be presented in any of the available formats, i.e., simple relevance, clustered (list or tree format), categorized, by simply selecting the button for the desired format, in addition to the per-site raw data view that is provided initially, as described above. The selections can be made in any order and the user may find it valuable to browse more than one format to help identify the most relevant information.

Figure 7:
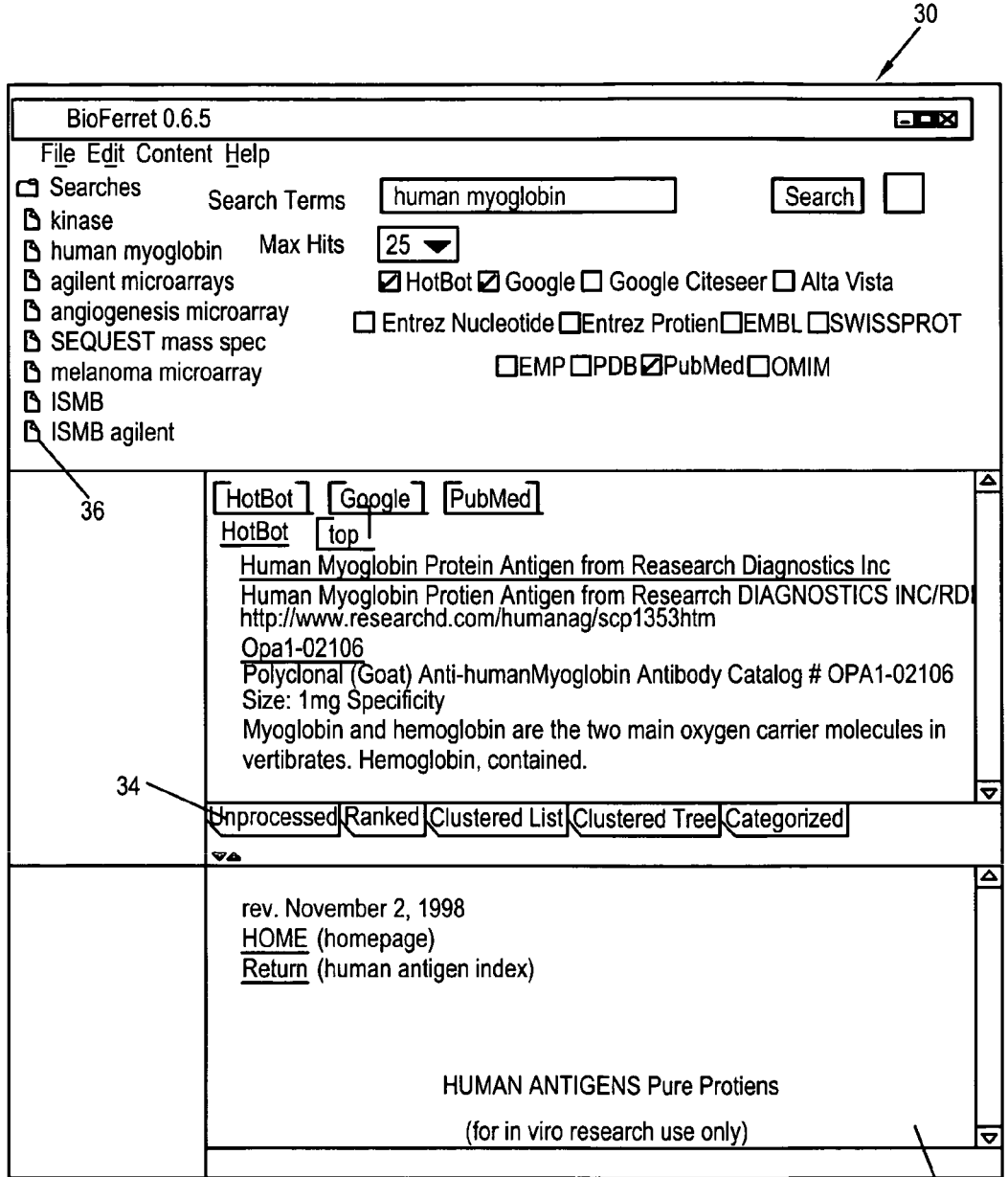
FIG. 7 shows an example of a screen display on a user interface which shows a query refinement feature.
Figure 8:
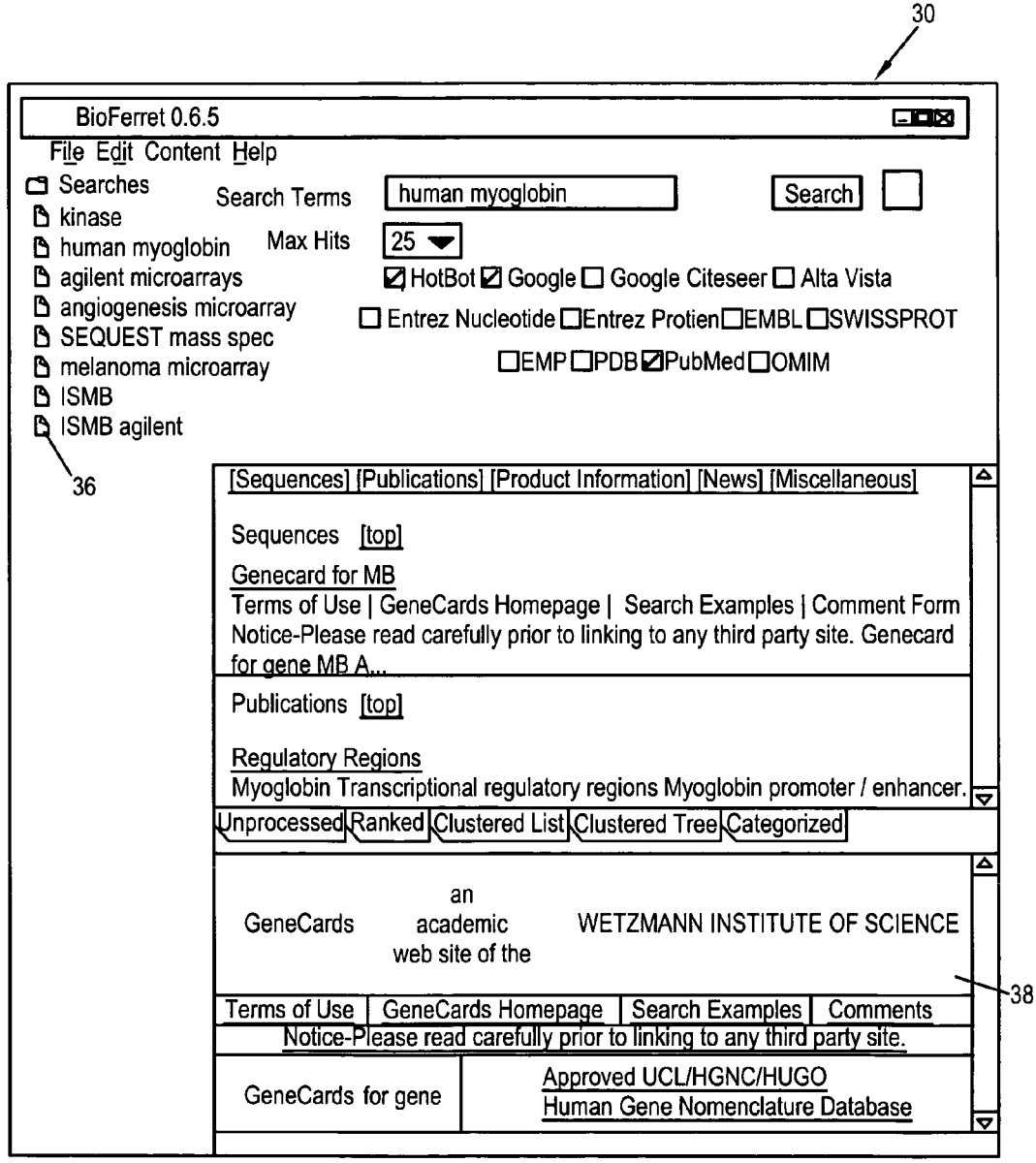
FIG. 8 shows an example of a screen display on a user interface which shows a Search Results Collection Browser.

FIG. 7 shows a display on user interface 30 of a further feature which may be employed with the present invention. A Query Refinement feature may be provided to effectively carry out a query within a query. For example, if a user has previously performed three or four searches relating to "human myoglobin", the results of these searches can each be saved to a local database. The stored searches can be displayed in a side window 36, as shown in FIGS. 7 and 8. The raw results view and the internal data structures corresponding to the entire results set are saved in the local database. When restoring the data from the local database, the ranking, clustering and categorization groupings are recalculated.

A sub-query or query refinement can then be conducted during a subsequent related search to obtain results from the stored results of the previous searches. The data mining module 20 can process results from the query refinement in the same manners as discussed above. Because the sub-query searches only presumably relevant information, and because the search is performed only on an internal database, this search can potentially return very relevant information in very little time.

As another feature, a Search Results Collection Browser may be included in the present system, as shown in FIGS. 7 and 8, wherein an integrated frame 38 on the user interface 30 puts an additional frame (in this case, an Internet Explorer frame) inside the system application (in this case, a Java application), to view all browser events going on. The Search Results Collection Browser includes a relevance feedback mechanism which analyzes the browsing to determine which document the user spends the most time with, to learn what relevant documents look like. Of course the term "relevant documents" is defined here by the user's tastes and needs, and, over the course of several to many searches, if a searcher tends to research a particular area of science, the relevance feedback mechanism will begin to associate recurrent themes of browsing and times spent with similar documents. Thus, based upon the user's historical preferences, a more sophisticated weighting algorithm can be developed by the Search Results Collection Browser to be applied as a weighting factor to documents being ranked in a current search and data mining operation.

The Search Results Collection Browser learns by watching browsing habits when using the metasearch and data mining system described herein. The browsing and time spent information is then used to predict subsequent relevance to search results. Hooks may be provided in the Search Results Collection Browser so that when a user clicks on or otherwise selects a document for examination, the document shows up in the Search Results Collection Browser window, and the hooks monitor the amount of time that the user spends looking at that document. The "hooks" are supplied by embedding an Internet Explorer frame within the application to be used as a "preview frame" 38. Internet Explorer exposes interfaces that can be called to provide notification whenever the user performs certain actions, to include opening a particular page for viewing. By such notification, the present invention can track how long a page is being displayed in the preview frame 38, as well as how much the user interacts with it.

This feature monitors any action in which the user clicks or drags on an area of the preview frame 38, such actions including accessing scroll bars, pop-up menus, internal hyperlinks, or even clicking on an inactive spot of the HTML page, for example. The time span and frequency with which the user "touches" this window (by clicking or dragging, for example)

may then be used as a metric of their interest in the page. If the user clicks on a hyperlink to launch a new page referenced by the previewed page, the new page is launched in an external window, which may optionally be tracked, but, by default, is not tracked. The more time or activity spent with a particular document, the heavier the weighting factor that will be applied to that document in a prospective search. Over time, the reliability of this type of weighting factor increases, as it becomes more accurate at predicting the types of documents that the user tends to look for.

Alternatively or additionally, the Search Results Collection Browser may also monitor, store and analyze browsing habits on a site specific basis. For example, if a user spends 80% of the search time accessing documents in a particular sequence database, more weight can be given to documents identified in a later search from that particular database.

In another aspect that may be provided with the Search Results Collection Browser, the Search Results Collection Browser may examine the contents of the document that the user is looking at and try to determine if the content is relevant. For example, the Search Results Collection Browser may attempt to determine whether the overall topic or content of the particular document pertains to what the user is currently searching for, or whether it is similar to the content of documents that are being searched for. A distance metric, such as that described with regard to the clustering function above may also be used here. In such a situation, the Search Results Collection Browser would compare the current document that the user is browsing with the saved contents of all the documents in the previous searches having been saved from past searches, to determine whether any other documents may be relevant with the current document so as to form a cluster.

Figure 9:
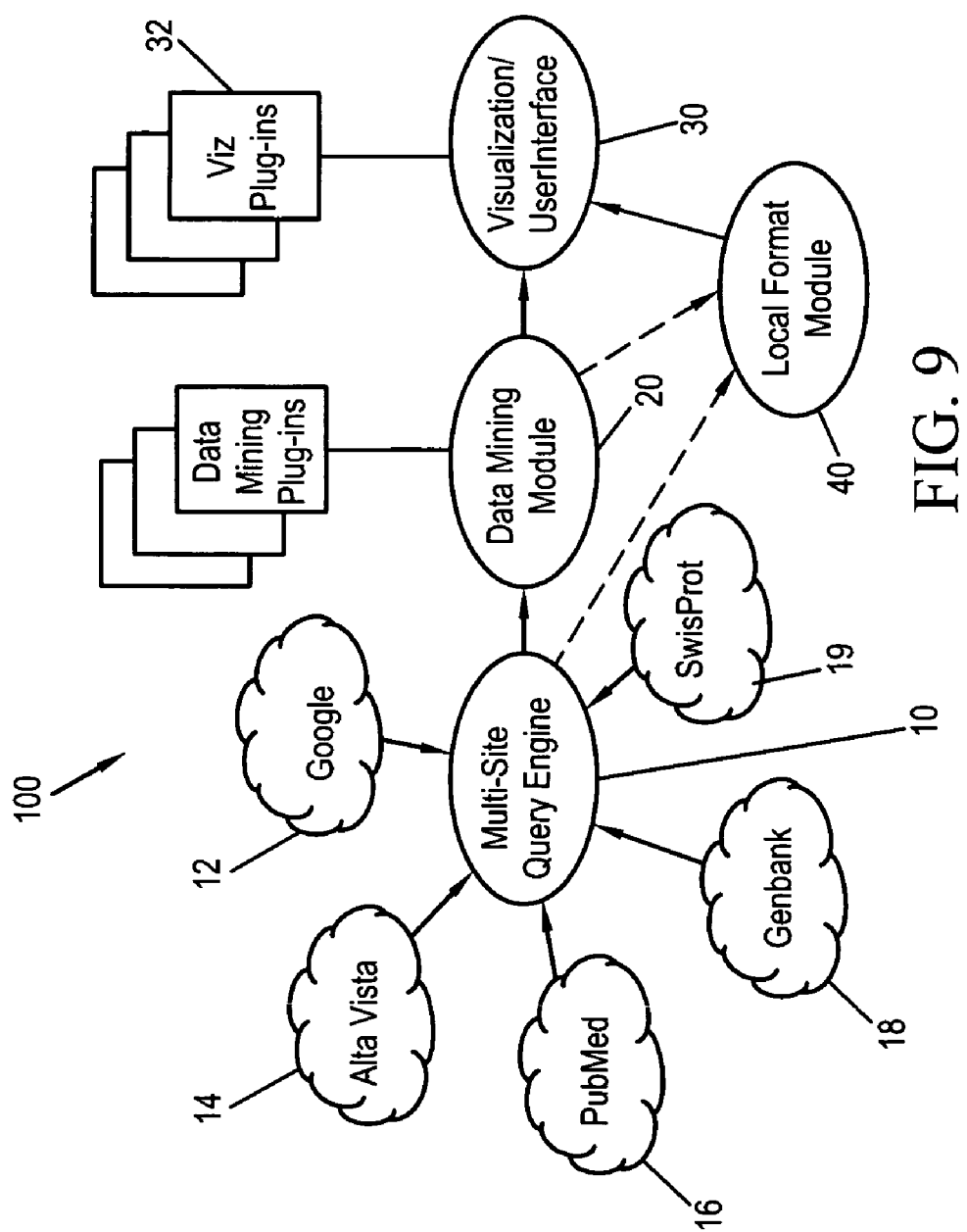
FIG. 9 shows an architectural schematic of a system according to the present invention including a local format module.

In addition to the data mining procedures described above, or alternative to all or a portion of the data mining procedures, local format module 40 may receive raw document data from the multi-site query engine or information outputted by data mining module 20, as shown in FIG. 9. Local format module 40 extracts relevant information (e.g., terms relevant to the query from the received information and converts the extracted information to the local format.

Additionally or alternatively, other terms that are not in the query, but are defined in one or more various user context files may be inputted to determine relevancy. Automated text mining techniques, whether by data mining module 20 or local format module 40 may be used to extract "nouns" (e.g., biological entities) and "verbs" (e.g., relationships) from the textual data received. From this, biological entities that are involved in a relationship can be identified (e.g., a promotion interaction involving two genes, etc.). These entities and relationships are converted to the local format that serves as an object model that can be manipulated in different ways, such as to construct biological diagrams, overlays, etc.

Once the entities and relationships have been converted to the local format, a diagram view/network visualization of the entities and relationships may be automatically generated by linking like entities, using the local format architecture, for example. Note that all documents retrieved by the query (or some subset thereof) may be automatically processed as described above, in batch mode. Alternatively, separate documents, clusters, or small subsets of documents and/or clusters may be processed sequentially, each time adding to the resultant network visualization by adding the current round of locally formatted entities and relationships to the previously constructed network diagram in the same manner as described above.

Alternatively or in addition to extracting relevant entities and interactions from the text based on the terms of the query, the system may identify entities and interactions base on one or more predefined user contexts (which may be user-editable), as noted above. A user context may include, for example, a list of keywords. Currently the present system is adapted to read text, XML or Excel files, although it would be apparent to one of ordinary skill in the art to extend the capability to other known formats. Each entry in the user context may include an identifier as to whether the entry is a noun or a verb; the name of the entry (i.e., which contributes to the lexicon for searching); the type that the entry is (e.g., cell, process, disease, or the like for nouns; bind, promote, inhibit, or the like for verbs); and aliases for the name of the entry, which may also be added to the lexicon. However, a user context may still function with only a subset of such information, although less effectively (e.g., aliases could be omitted for some entries). Of course further descriptive information categories could be included for characterizing one or more entries in the user context, as would be readily apparent to one of ordinary skill in the art.

Figure 10:
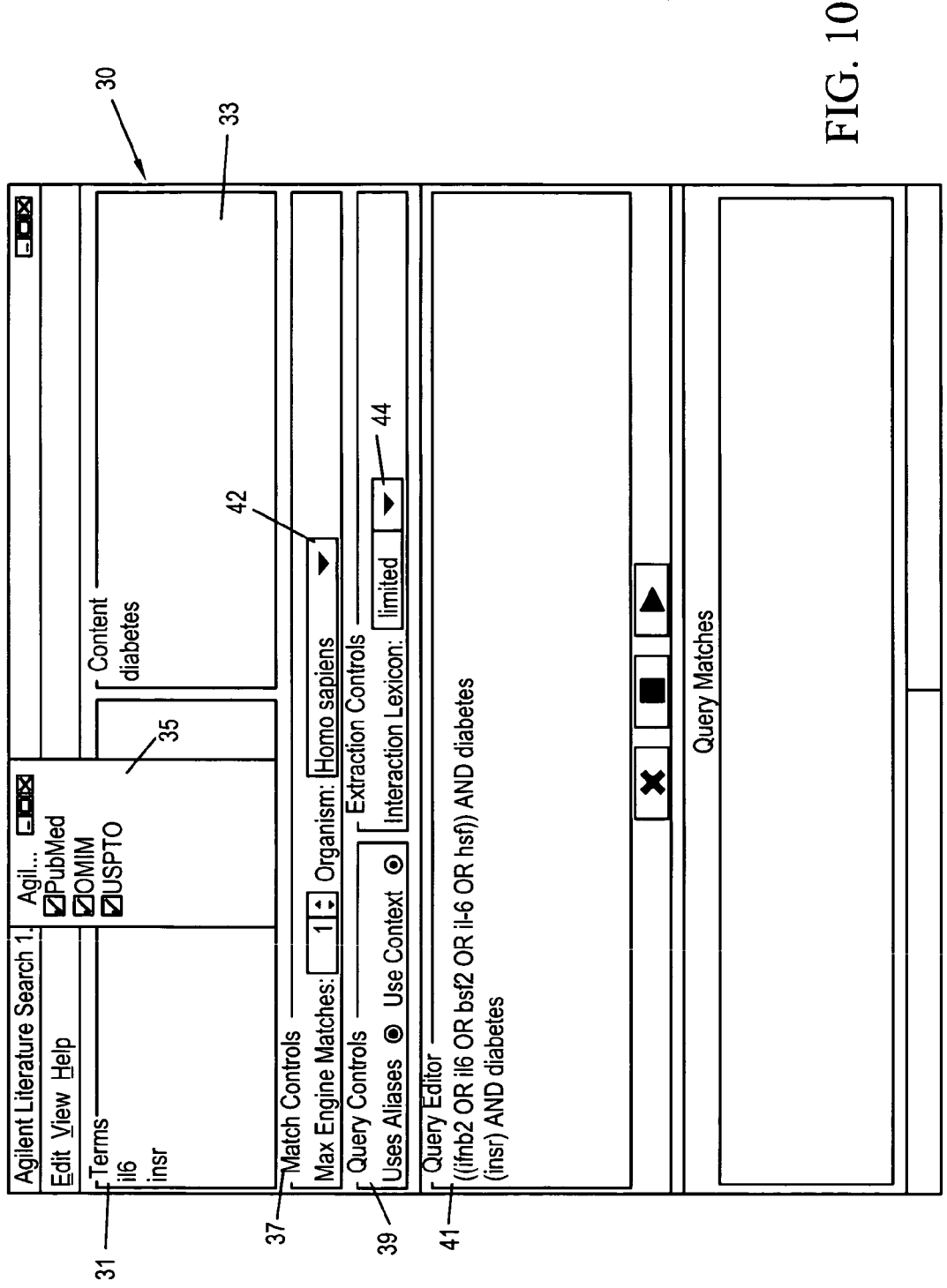
FIG. 10 shows a user interface configured with user inputs for performing a metasearch.

FIGS. 10-13B illustrate an example of automatic extraction of entities and interactions from text and automatic generation of a biological diagram after conversion of the extracted entities and interactions to a local format. FIG. 10 shows user interface 30 where term "il6" and "insr" have been entered into the search terms window 31 to define the queries to be performed. The term "diabetes" has been inputted to the "Context" window 33. As such, the context term "diabetes" is added with a Boolean "AND" connector to each of the query terms "il6" and "insr" to further define the queries to be performed. Note that the "context" terms in context window 33 are not to be confused with the earlier described "user context". The user context files are not visible in FIG. 10, but are selectable via the tabs 42 and 44, which link to nouns (noun file or files) in the user context and verb file or files in the user context to be used, respectively. Thus, the noun file or files may contain the names and aliases of interesting nouns (e.g., gene names and aliases as defined for humans in this example, based on Entrez Gene, a public database at http://www.ncbi.nlm.nih.gov/entrez/query.fcgi?db=gene) and the "limited" interaction lexicon 44 refers to a choice of a verb lexicon (user context verb filed) to be used.

A wide set of choices can be provided for noun lexicons as well as verb lexicons, as many files may be defined from which to select as user context. In the present example, there are two choices: (i) Limited and (ii) Relaxed. The limited choice has a smaller and more restricted set of verbs in the verb file, whereas as the relaxed choice allows for many more verbs. Therefore, a lot more interactions will be extracted with the "Relaxed" choice than with the "Limited" choice. Users can modify either of the two verb files according to the verbs they deem as interesting. As an example, the Limited file is strictly restricted to the following five verbs (and their common synonyms): activate, bind, inhibit, cleave, and catalyze. The Relaxed choice allows for a number of other verbs. For example, the Relaxed file in this instance includes: activat, enhance, promot, hasten, accelerat, augment, induc, stimulat, increase, require, incit, upregulat, up-regulat, up regulat, breakdown, breakbond, bind, assembl, join, attach, bound, links to, links with, linked to, linked with, cleav, form complex, destabilize, caus, based on, due to, result in, contain, container, createbond, conjugat, stabiliz, acetylat, methylat, phosphorylat, generat, express, correlate, accumulate, produc, overexpress, inhibit, inactivat, degrad, repress, suppress, abolish, block, downregulat, down-regulat, down regulat, prevent, reduce, decreas, modif, mutat, process, react, interact, mediat, release, disassembl, discharge, signal, regulat, modulat, substitute, replac, and catalys; wherein the base terms extract exact matches as well as those terms that match and have an additional suffix. These files may be edited by a user. Additionally, other files may be included as choices for interaction lexicons, as well as noun lexicons.

In this example, there were ten different organisms from which to select as the selected organism (noun file). Each noun file in this example contains the gene names and aliases as defined in the Entrez Gene database. Further, a few user defined names and aliases were also added to the Homo sapiens and Mus musculus organism files.

Three search engines have been selected for performance of the metasearch, as shown in the Search engines window 35. The maximum number of documents from each search engine per query was set to "1" under the user definable "match Controls" window 37. Aliases were considered while performing the metasearch and the context term "diabetes" was included as noted by selection of "Use Aliases" and "Use Context", respectively, in the Query Controls window 39. The search string resulting from inclusion of aliases and context terms with regard to the search terms is displayed in the query editor 41.

Figure 11:
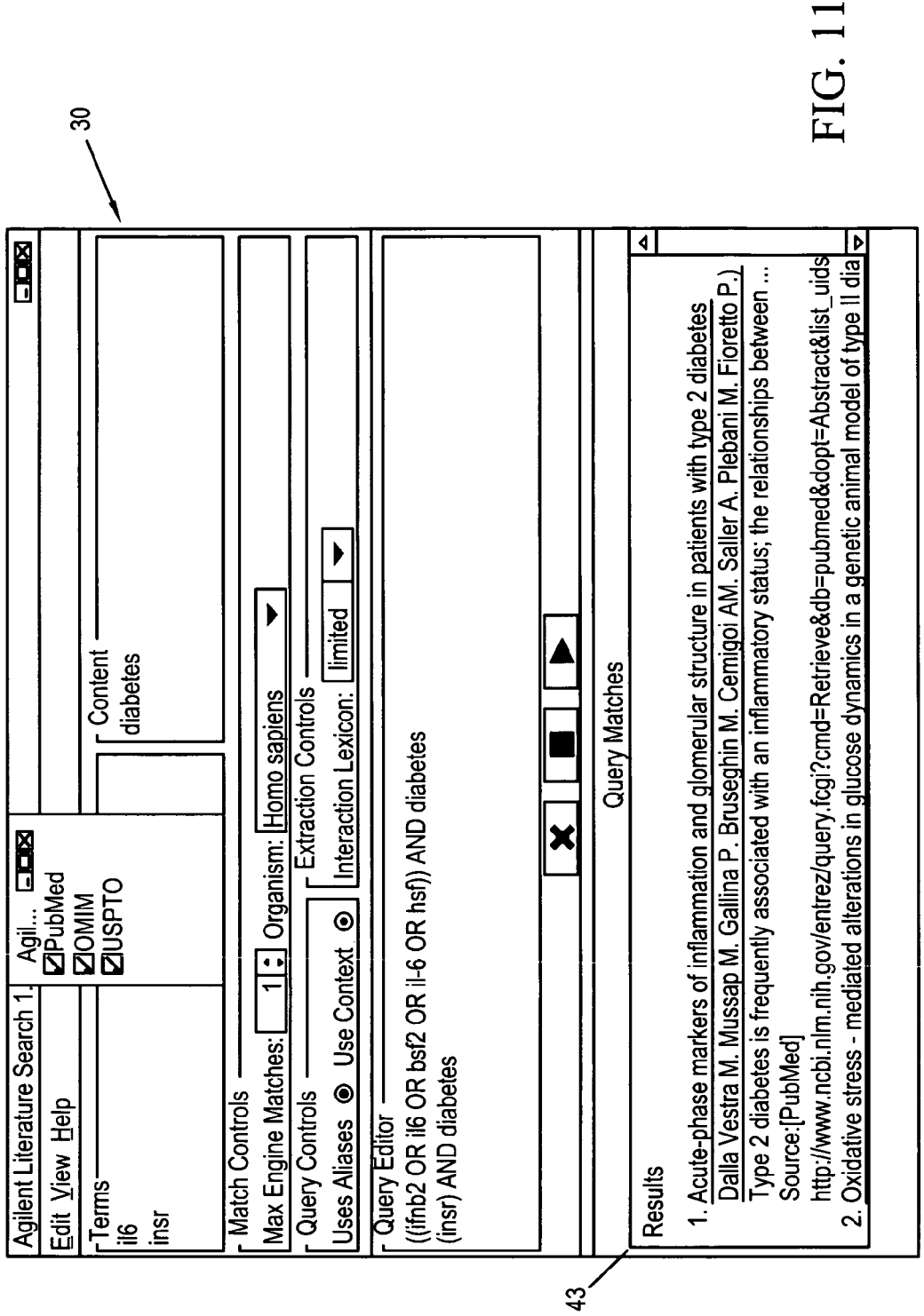
FIG. 11 shows the user interface of FIG. 10 after performance of a metasearch, wherein results are displayed.

In response to running the metasearch as defined in FIG. 10, the system fetched six documents (the documents found to be most highly relevant to the search settings, one document per each search term (il6 or insr) per search engine (PubMed, OMIM or USPTO), a portion of which are displayed in the "Query Matches" window 43 in FIG. 11. Note that the entire list can be viewed by scrolling through it, using scroll bar 45, for example.

Figure 12A:
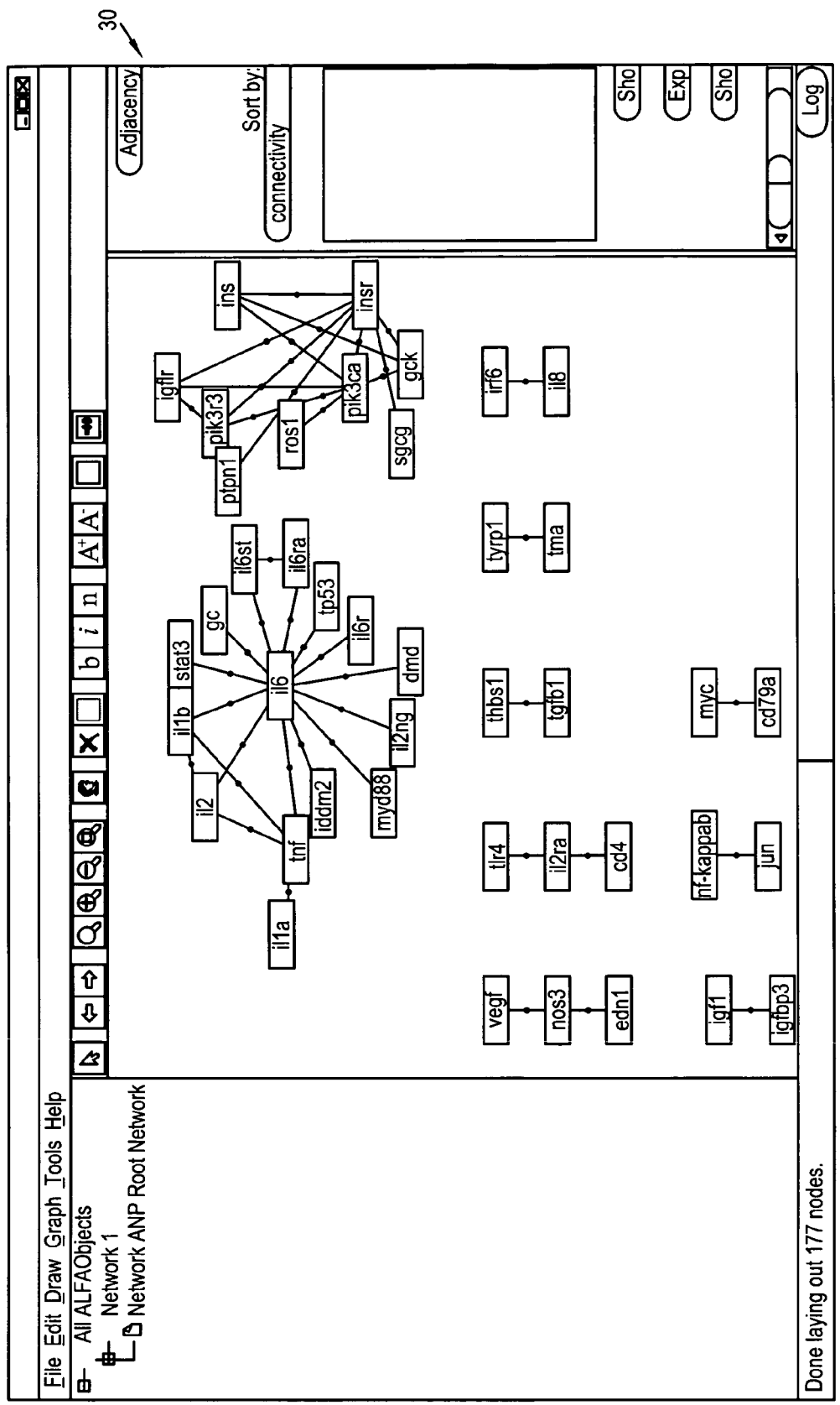
FIG. 12A shows an example of a diagram visualization produced by the system.
Figure 13A:
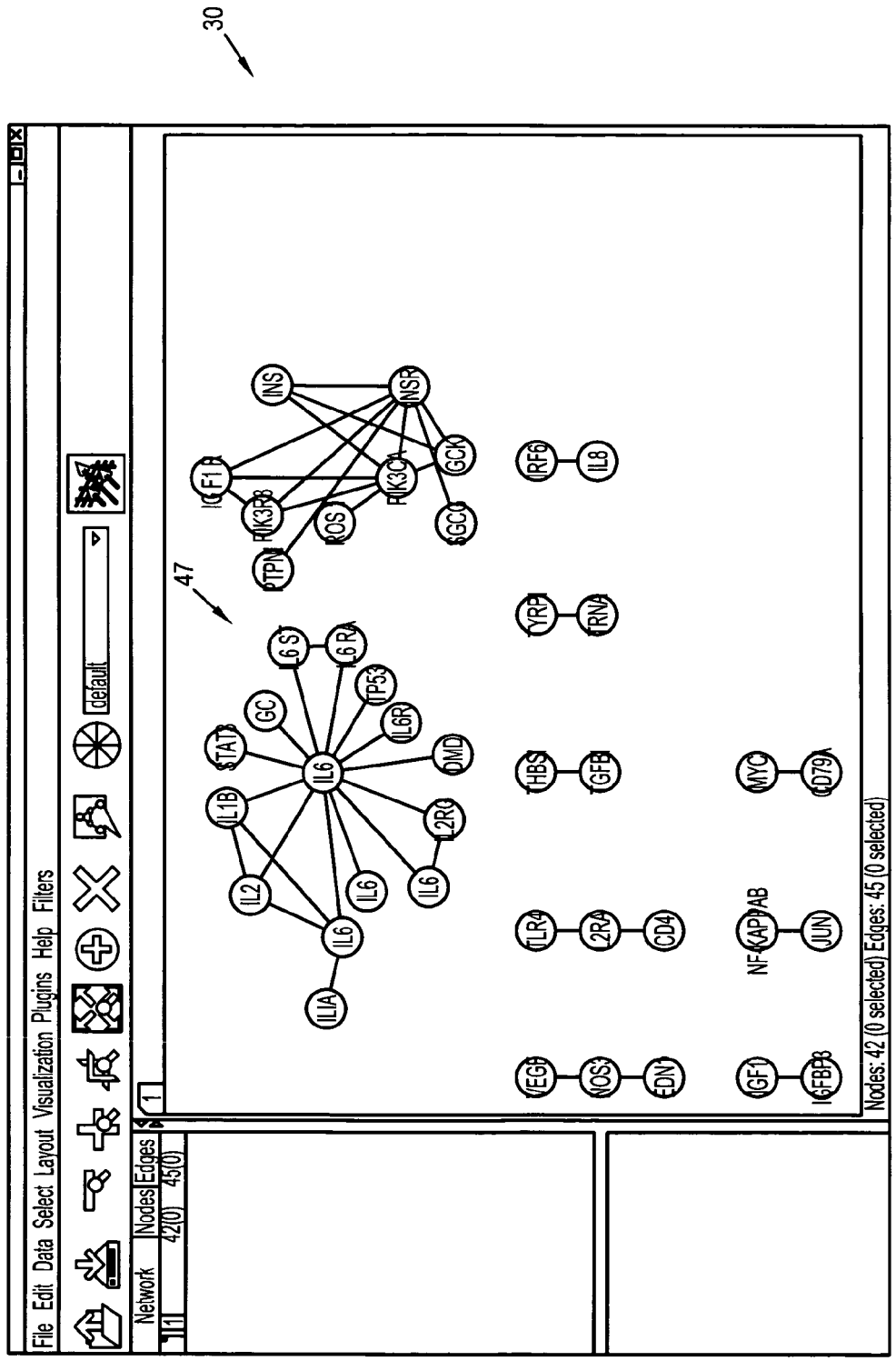
FIG. 13A shows another example of a diagram visualization produced by the system.

The system fetches raw results (e.g., the text of the documents identified in query matches window 43) and then uses locally stored user context files (these are the nouns and verbs of interest to the user, e.g., the Organism and Interaction lexicons 42 and 44, respectively) as a basis for extracting one or more of the interesting nouns and verbs, contained in one or more user context files, from individual sentences in the raw documents resulting from the metasearch. The extracted noun(s) and/or verb(s) are then converted to a local format, as described previously. All of the extracted terms may be stored in a single local format file, which may be an XML file or the like. The local format file may then be visualized as a biological diagram as network visualization 47 on user interface 30. FIG. 12A shows an example of a network visualization 47 for the results of the query term "il6" as defined in FIG. 10, using software provided with the system. Alternatively, the network visualization 47 maybe visualized using a visualization plug-in 32, such as another visualization software package, open source visualization software or the like (e.g., Cytoscape (http://www.cytoscape.org/). FIG. 13A shows an example of the network 47 produced for "Il6" as visualized using a plug-in 32.

Figure 12B:
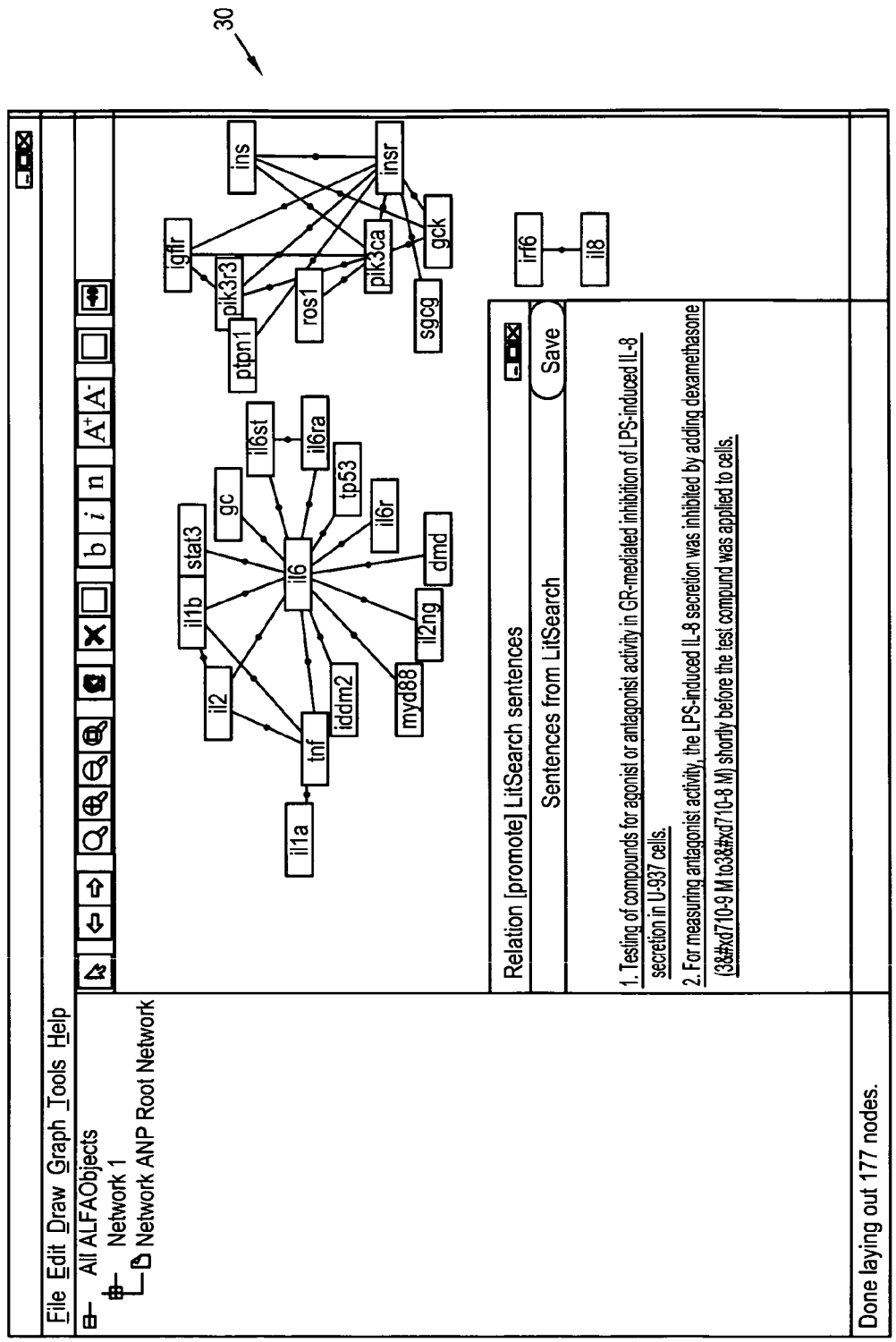
FIG. 12B shows the diagram visualization of FIG. 12A, together with visualization of the relevant sentences of the textual documents from which the interesting terms were extracted for conversion to the local format and generation of the diagram visualization.
Figure 13B:
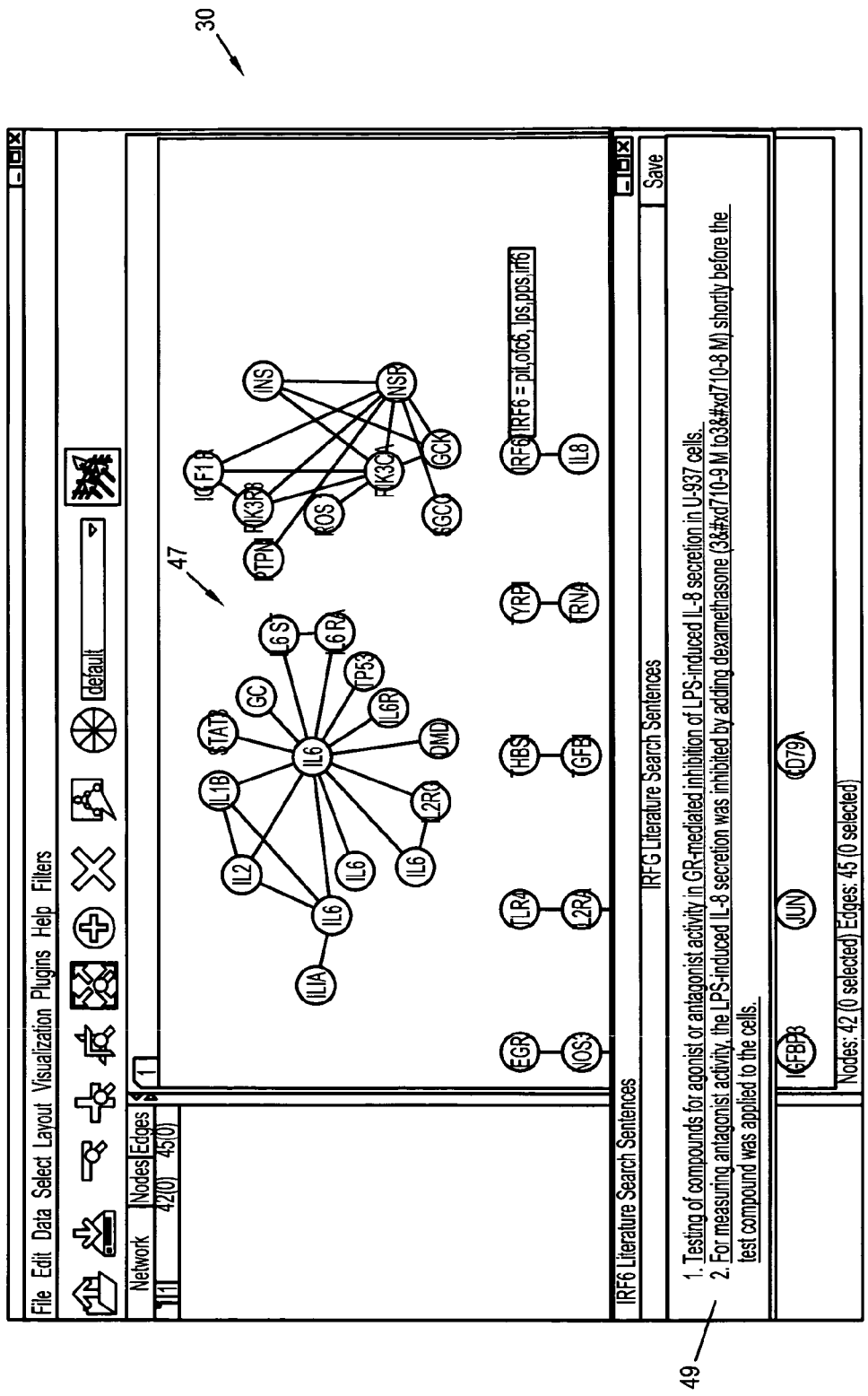
FIG. 13B shows the diagram visualization of FIG. 13A, together with visualization of the relevant sentences of the textual documents from which the interesting terms were extracted for conversion to the local format and generation of the diagram visualization.

Additionally, the relevant sentences of the textual documents from which the interesting terms were extracted for conversion to the local format and generation of a diagram visualization may be displayed in the "Relation" window 49 as illustrated in FIGS. 12B and 13B.

In summary, the automatic extraction process takes as input the text in the document and a list of user context terms (these are either passed to local format module 40 or local format module 40 reads directly from one or more text, XML, or Excel files). The text may be broken down into individual sentences. Words in each sentence are checked against the user context terms to identify relevancy/interestingness. If a sentence has more than one interesting noun and at least one interesting verb, then an interaction may be created between these nouns and stored into the local format. Based on certain heuristics, each interaction may be associated with an interaction type (e.g., if there is only one interesting verb, promote, then the interaction type "activate" may be assigned). In case of multiple verbs, any interaction type may not be determined, but set as "unknown". Further disambiguation processing may be carried out in these instances, as noted below. For each interaction stored in the local format, a reference to the interaction in terms of the sentence and the source (URL link of the document) may be stored with the interaction. Once all the documents have been processed, the local format objects are sent to a visualization tool as noted above and displayed.

Additionally or alternatively to the automatic generation of a biological diagram as described above, the system may automatically or semi-automatically (such as when a user selects this function, for example) rank and/or filter the raw data search results based on the linking of the relevant data extracted therefrom and converted to the local format, with a pre-existing locally formatted data set that matches the relevant data to a greater or lesser extent. The ranked and/or filtered results may be displayed in the query matches window 43, for example along with ranking scores, which may be normalized, like those shown in FIG. 3. As noted, these results may be visualized with or without visualization of a network diagram 47.

After converting the extracted relevant data to the local format in a manner as described above, the local formatting expresses the relevant data in a way that allows direct comparison with one or more other data sets formatted in the local format. Thus the local format module 40 may link the locally formatted data which was converted from the relevant data extracted from the scientific text, with any other information existing in the user's system in the local format that matches the converted scientific data. In this regard, it should be noted that the user's experimental data, or whatever data is desired to evaluate/compare with the scientific text data, has already been converted to the local format, either automatically, semi-automatically or manually, as described in co-pending, commonly owned application Ser. No. 10/154,524, filed May 22, 2002 and titled "System and Methods for Extracting Pre-Existing Data From Multiple Formats and Representing Data in a Common Format for Making Overlays". However, if the user's data has not yet been converted, it can be converted to the local format after converting the scientific text data. In either case, after both datasets have been placed into the common local format, the linking may be performed.

The links provide information that can be used in ranking, and otherwise discriminating the scientific textual data in a way that is directly related to the user's own experimental data or other data on the user's system. In this way, the results are much better tailored according to the context of what the user is searching for, not just according to the words of a query and comparison of scientific text documents against one another. For example, if a first scientific text document mentions both gene A and gene B in a mechanism relating to gene C, whereas a second scientific document relates to an up-regulation of gene B by gene A, ranking and other ordering according to only a query regarding both genes A and B, and comparison among the scientific articles would rank articles 1 and 2 equally. However, if the user has experimental data which is directed to regulation of gene B by gene A, the present invention would rank scientific text article 2 much higher than article 1, since the local formatting of article 2 would be linked to the local formatting of the user's experimental data, whereas article 1's local formatting may only be linked to the experimental data by the nouns (gene A, gene B) associated with the datasets, if linked at all.

The user may be given the option to rank the scientific text articles (or subset of the articles, if the user wishes to process only a portion of the retrieved articles at one time) according to their relevance. Relevance rankings may be predicated upon the number of links that each particular document (or portion of a document, as described below) has with the user's data of interest. Thus, whenever genes, proteins or whatever entity or entities the experimental data is dealing with is mentioned, those documents that mention more of them are ranked higher than those with less mention. Further, the verbs that describe the pre-existing data and which are linked with verbs in the local formatting of a scientific document also contribute to the ranking score. In fact, the verbs may be given a different weighting factor than the nouns, if desired, so that they count differently towards the ranking of a scientific text document.

The ranking may be carried out on a per document basis, which may be user selectable, or, as an alternative, the user may select to rank the material according to paragraphs of the textual data, or other smaller relevant portions of a document, such as sentences, or a predefined number of words around the relevant nouns or verbs. In this way, the present invention can more accurately hone in and identify a particular portion of a scientific text document which describes or relates to the data of interest. This option is particularly useful in situations where a scientific article is relatively lengthy, but only a small portion of the article is relevant to the user's pre-existing data. When a large number of documents are being ranked, and a large number of documents are similar in their relevance, this feature can also be useful and save a lot of time, allowing the user to go directly to the relevant information in each document.

It is further noted that the ranking procedures need not be exclusive of one another. That is, even after ranking by documents, the user can choose to further rank according to paragraphs or relevant portions of the documents. For example, if a user is looking at cancer and two particular genes, then if a scientific text talks about cancer and those two genes in a particular paragraph, that paragraph will be highly ranked, and can be brought up, even within the scientific text on user interface 30. If the document containing the highly relevant text is large, e.g., a large journal article, then the user can save a great deal of browsing time by being able to zero in on the particular location of the relevant text within the large article. Those paragraphs which are most interesting (i.e., relevant, have more links to the experimental data) are ranked higher within the text than the other paragraphs.

As noted above, the ranking processing of the scientific text data is based on some rendition of the local context, which, in its simplest form, could be simply nouns and verbs. In such a situation, the user may have experimental data expressed in terms of nouns and verbs (e.g., local format). In ranking, the present invention uses a processing engine to process the nouns and verbs of interest, and look for them in the scientific text documents, as has already been described. The scientific text documents, which may be numerous, are realigned by the processing engine which finds matches of the nouns and verbs in the scientific text. The ranking may be done according to document, according to relevant passages or paragraphs within documents, or according to document, with an additional ranking of paragraphs/passages within each document.

Additionally or alternatively to ranking the data as described above, the system may filter the data (such as when this function is selected by the user, for example). Filtering can be an extremely useful tool in situations where the user wants to more specifically examine only a portion of the pre-existing data that is linked with the scientific textual documents, for example. Filtering is also useful for removing search results data that is not linked with the pre-existing data, thereby simplifying the results to be reviewed by the user. As an example of the former, if the pre-existing data contains experiments and relationships regarding genes A, B, C and D, the user may be interested only in examining relationships between genes A and B at that moment. Even if a general query is done specific to only genes A and B, some of the scientific journal articles may also contain information regarding gene C and/or gene D, even if only incidentally. In such a situation, the local format module could form links between the local formatting of the experimental data pertaining to genes C and D and the description of these genes in the scientific text articles.

In order to filter out the extraneous data regarding genes C and D, the user can select a subset of the local formatting of the pre-existing data to be considered for linking. In this instance, for example, the user could select to process only genes A and B and the relationships therebetween. Then the local format module 40 processes that subset of the local formatting of the pre-existing data against the local formatting of the scientific text documents. If there were documents relating only to gene C or to gene D or to genes C and D, these documents will be filtered out as a result of such processing, and therefore not displayed as results in the user interface 30. Ranking may be performed prior to filtering, after filtering, or not at all when filtering.

Alternatively or additionally to the automatic processing described above, the system 100 may provide user-interactive tools via user interface 30 to facilitate disambiguation of relationships where needed. Because it may be difficult to determine directionality of relationships/interactions identified solely through the use of natural language programming techniques, the user may be involved in disambiguating the relationships, as noted above. Once interactions have been disambiguated, the user can select all or a portion of the disambiguated relationships listed, and a diagram view of the relationships is generated by linking like entities, using the local format architecture, for example. It should also be noted here, that a diagrammatic view can be generated, either automatically, as described above, or by user selection of entities and relationships to be represented into the diagrammatic view, prior to disambiguating all information and the disambiguation process can be performed on the diagram view, using techniques described above, as well as in application Ser. No. 10/641,492.

The disambiguation process may be performed sequentially, on a document-per-document basis, with subsets of documents or clusters, or as a batch, considering all returned documents. When working sequentially, after disambiguation of a first document/group of documents, the user may then wish to import another abstract, textual document, or a portion thereof, or group of documents and iterate the process described above. After disambiguation of interactions/relationships in this next round, relationships and entities which are common to those identified in previous textual documents can be identified, either automatically or manually, and this information may be joined to the previously created biological diagram, via use of the local format.

Disambiguation can be performed with respect to each document, as the documents may not always agree as to the mechanism of an interaction. Where there is disagreement, upon generating a graphical diagram, the diagram will indicate such discord. As a simple example, if a first document indicates that entity A increases entity B, while a second article indicates that entity A decreases entity B, then the graphical representation may show a block for A, a block for B, and two lines extending between A and B. The lines may be differentiated by color coding (e.g., one green and one red) and/or by different arrowheads pointing towards B, e.g., one with an arrow-shaped arrowhead (i.e., ──→) for a promotion and one with a blocked arrowhead (i.e., - - - |) to indicate an inhibition, for example. Other visual differentiators may be used in addition to, or alternatively to those described.

When more than one document contains an interaction that is displayed in a graphical diagram, annotations may be made to that portion of the diagram which link that interaction to each of the documents where it occurs. Thus, not only is that interaction linked directly, such a by a hyperlink, but other annotations may be included to suit the user's needs, such as described for example in application Ser. Nos. 10/155,304, 10/155,616 and 09/863,115.

Figure 14:
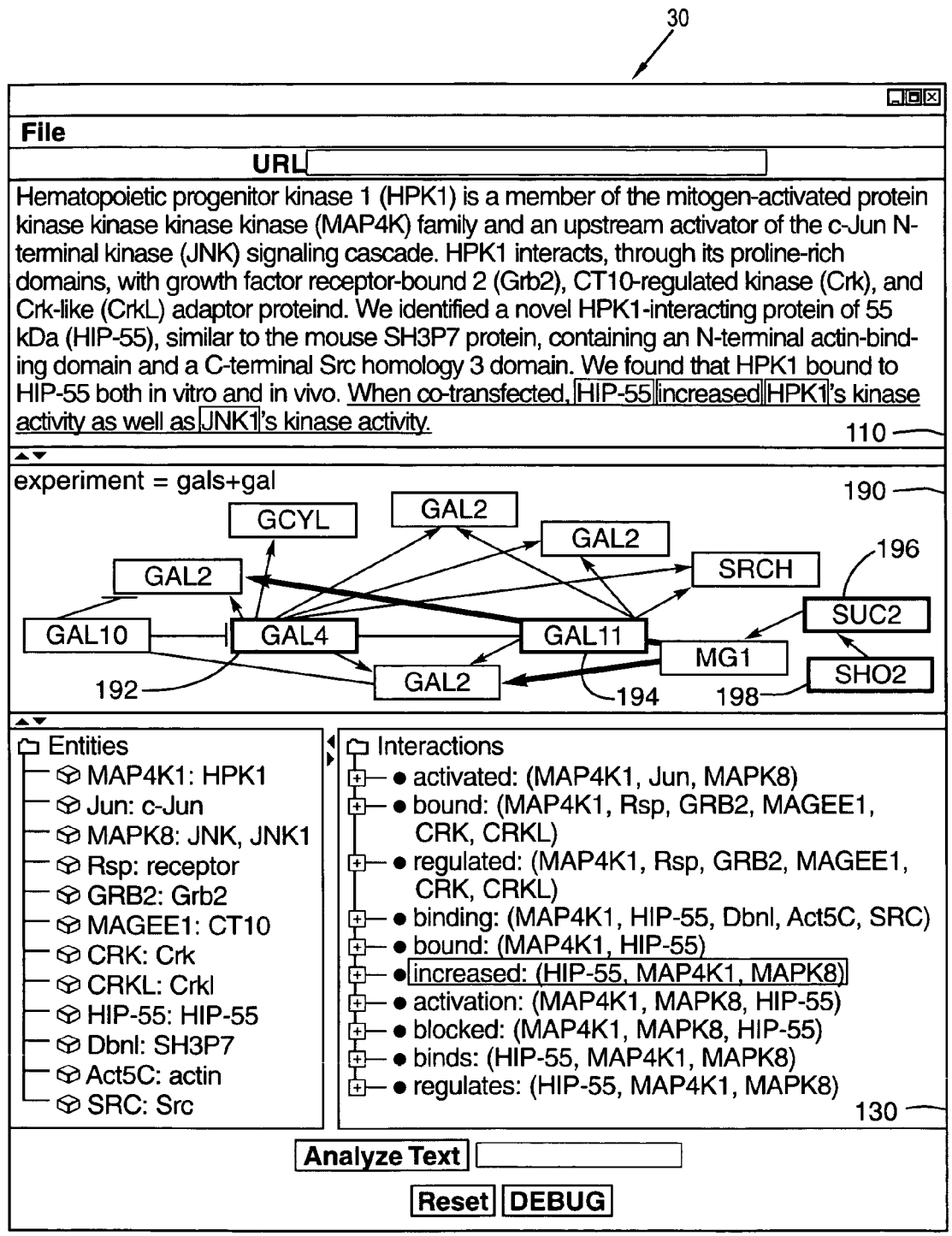
FIG. 14 shows a user interface displaying text, entities and interactions from which network diagrams may be automatically, semi-automatically or manually constructed.

Thus, the present invention further provides the ability to build networks of interactions by composing entities, interactions, and diagrams. Using this feature, the user may select a subset of interactions in the "Interactions" list 130 and drags them into a separate network viewer window 190, as shown in FIG. 14. Alternatively, the selected interactions may be automatically populated into viewer window 190 upon their selection. The system may merge interactions with common entities, forming a graph structure.

The graph structure can be built upon by analyzing an additional textual document and processing it as described above with regard to the first textual document. Upon identifying and disambiguating the interactions in the second textual document, these interactions can then be joined in the graphical composition. This type of building can be done repeatedly with as many textual documents as desired. Alternatively, batch mode, automatic processing may be performed such that user interface 30 automatically displays a network diagram upon receiving entities and interactions having been automatically extracted and converted to the local format by local format module 40.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, system, system component, processor, process step or steps, to the objective, spirit and scope of the present invention. All such modifications are intended to be within the scope of the claims appended hereto.

That which is claimed is:

1. A computer implemented method of performing a domain-specific metasearch, and obtaining search results therefrom, said method comprising:
   providing a metasearch engine capable of accessing generic, web-based search engines and domain-relevant search engines;
   receiving one or more queries inputted by a user to the metasearch engine and searching for documents on at least one of said generic, web-based search engines and domain-relevant search engines which are relevant to the queries;
   fetching raw data search results in the form of text documents from each of said at least one of said generic, web-based search engines and domain-relevant search engines;
   extracting relevant data including semantic information from the raw data search results;
   converting the relevant data, including the semantic information, to a local format; and
   displaying the relevant data having been converted to the local format as a network display for viewing by a user.

2. The method of claim 1, wherein said displaying is performed on a user interface.

3. The method of claim 2, further comprising displaying the raw data on the user interface while said extracting and converting are being carried out.

4. The method of claim 1, wherein said extracting, converting and displaying are performed automatically without user interaction.

5. The method of claim 1, further comprising disambiguating relationships in the relevant data by user interaction.

6. The method of claim 1, wherein said extracting is based at least in part on a predefined user context.

7. The method of claim 1, wherein said searching is performed on a selected set of said generic, web-based search engines and domain-relevant search engines.

8. The method of claim 1, wherein said domain-specific metasearch is directed to a life sciences domain.

9. The method of claim 1, wherein the network display is made up only of relevant data having been converted to the local format that has been selected by the user.

10. The method of claim 1, wherein said extracting and converting are performed only on data having been selected by the user.

11. A system for performing a domain-specific metasearch, and obtaining search results therefrom, said system comprising:
   a metasearch engine capable of accessing generic, web-based search engines and domain-relevant search engines, wherein upon receiving one or more queries inputted by a user, said metasearch engine searches for documents on at least one of said generic, web-based search engines and domain-relevant search engines which are relevant to the queries, and fetches raw data search results in the form of text documents from each of said at least one of said generic, web-based search engines and domain-relevant search engines;
   a local format module configured to extract relevant data including semantic information from the raw data search results and convert the relevant data, including the semantic information, to a local format; and
   a user interface including a screen said user interface configured to display the relevant data having been converted to the local format as a network display on said screen.

12. The system of claim 11, further comprising a data mining module configured to extract relevant data from the raw data search results and calculate additional statistical characterizations of at least one of the extracted relevant data and documents from which the relevant data was extracted.

13. The system of claim 11, wherein said user interface comprises means for user disambiguation of relationships in the relevant data.

14. The system of claim 11, further comprising a predefined user context, wherein said extracting is based at least in part on said predefined user context.

15. The system of claim 11, wherein said metasearch engine is configured for domain-specific metasearching directed to a life sciences domain.

16. A computer implemented method of performing a domain-specific metasearch, and obtaining search results therefrom, said method comprising the steps of:

providing a metasearch engine capable of accessing generic, web-based search engines and domain-relevant search engines;

receiving one or more queries inputted by a user to the metasearch engine and searching for documents on a selected set of said generic, web-based search engines and domain-relevant search engines which are relevant to the queries;

fetching raw data search results in the form of text documents from each member of the selected set;

extracting relevant data including semantic information from the raw data search results;

converting the relevant data including semantic information from raw results to a local format;

linking the relevant data in the local format with pre-existing, locally formatted data set which matches the relevant data;

at least one of ranking and filtering the raw data search results based on said linking the relevant data; and displaying the raw data having been ranked and/or filtered for viewing by a user.

17. The method of claim 16, wherein said displaying is performed on a user interface.

18. The method of claim 16, further comprising displaying the raw data on a user interface while said extracting and converting are being carried out.

19. A computer implemented method of performing a domain-specific metasearch, and obtaining search results therefrom, said method comprising the steps of:

providing a metasearch engine capable of accessing generic, web-based search engines and domain-relevant search engines;

receiving one or more queries inputted by a user to the metasearch engine and searching for documents on a selected set of said generic, web-based search engines and domain-relevant search engines which are relevant to the queries;

fetching raw data search results in the form of text documents from each member of the selected set;

extracting relevant data including semantic information from the raw data search results;

converting the relevant data including semantic information from raw results to a local format;

linking the relevant data in the local format with a pre-existing, locally formatted data set which matches the relevant data; and displaying the linked relevant data and pre-existing, locally formatted data that matches, as a network display.

20. The method of claim 19, further comprising ranking the raw data based on links set up by said linking.

21. The method of claim 20, further comprising displaying results of said ranking in a user interface.

22. The method of claim 20, further comprising comparing said relevant data to the data in said pre-existing, locally formatted data set, based on links set up by said linking.

23. A computer readable medium carrying one or more sequences of instructions for performing a domain-specific metasearch, and obtaining search results therefrom, wherein execution of one or more sequences of instructions by one or more processors causes the one or more processors to perform a process comprising:

receiving one or more queries inputted by a user to a metasearch engine and searching for documents on at least one of a generic, web-based search engine and a domain-relevant search engine which are relevant to the queries;

fetching raw data search results in the form of text documents from each of said at least one of said generic, web-based search engines and domain-relevant search engines;

extracting relevant data including semantic information from the raw data search results;

converting the relevant data, including the semantic information, to a local format; and displaying the relevant data having been converted to the local format as a network display.

24. A computer readable medium carrying one or more sequences of instructions for performing a domain-specific metasearch, and obtaining search results therefrom, wherein execution of one or more sequences of instructions by one or more processors causes the one or more processors to perform a process comprising:

receiving one or more queries inputted by a user to a metasearch engine and searching for documents on a selected set of generic, web-based search engines and domain-relevant search engines which are relevant to the queries;

fetching raw data search results in the form of text documents from each member of the selected set;

extracting relevant data including semantic information from the raw data search results;

converting the relevant data including semantic information from raw results to a local format;

linking the relevant data in the local format with a pre-existing, locally formatted data set which matches the relevant data; and displaying the linked relevant data and pre-existing, locally formatted data that matches, as a network display.

25. A computer readable medium carrying one or more sequences of instructions for performing a domain-specific metasearch, and obtaining search results therefrom, wherein execution of one or more sequences of instructions by one or more processors causes the one or more processors to perform a process comprising:

providing a metasearch engine capable of accessing generic, web-based search engines and domain-relevant search engines;

receiving one or more queries inputted by a user to the metasearch engine and searching for documents on a selected set of said generic, web-based search engines and domain-relevant search engines which are relevant to the queries;

fetching raw data search results in the form of text documents from each member of the selected set;

extracting relevant data including semantic information from the raw data search results;

converting the relevant data including semantic information from raw results to a local format;

linking the relevant data in the local format with a pre-existing, locally formatted data set which matches the relevant data;

at least one of ranking and filtering the raw data search results based on said linking the relevant data; and displaying the raw data having been ranked and/or filtered.

* * * * *

UNITED STATES PATENT AND TRADEMARK OFFICE
CERTIFICATE OF CORRECTION

PATENT NO. : 7,519,605 B2
APPLICATION NO. : 11/166696
DATED : April 14, 2009
INVENTOR(S) : Vailaya et al.

It is certified that error appears in the above-identified patent and that said Letters Patent is hereby corrected as shown below:

In column 22, line 4, in Claim 1, delete "display" and insert -- display, --, therefor.

In column 23, line 15, in Claim 16, delete "with" and insert -- with a --, therefor.

Signed and Sealed this

Thirtieth Day of June, 2009

JOHN DOLL
*Acting Director of the United States Patent and Trademark Office*